US006800852B2

(12) United States Patent
Larson et al.

(10) Patent No.: US 6,800,852 B2
(45) Date of Patent: Oct. 5, 2004

(54) NONDESTRUCTIVE CHARACTERIZATION OF THIN FILMS USING MEASURED BASIS SPECTRA

(75) Inventors: Paul E. Larson, Bloomington, MN (US); David G. Watson, Eden Prairie, MN (US); John F. Moulder, Bloomington, MN (US)

(73) Assignee: ReVera Incorporated, Sunnyvale, CA (US)

( * ) Notice: Subject to any disclaimer, the term of this patent is extended or adjusted under 35 U.S.C. 154(b) by 0 days.

(21) Appl. No.: 10/330,383

(22) Filed: Dec. 27, 2002

(65) Prior Publication Data

US 2004/0135081 A1 Jul. 15, 2004

(51) Int. Cl.$^7$ ............................................. G01N 23/00
(52) U.S. Cl. ........................................ 250/305; 438/50
(58) Field of Search ............................... 250/305–307; 378/50, 88–90

(56) References Cited

U.S. PATENT DOCUMENTS

| | | | | |
|---|---|---|---|---|
| 3,766,381 A | * | 10/1973 | Watson | 250/305 |
| 3,772,522 A | * | 11/1973 | Hammond et al. | 250/305 |
| 4,048,498 A | * | 9/1977 | Gerlach et al. | 250/305 |
| 4,810,880 A | * | 3/1989 | Gerlach | 250/305 |
| 5,280,176 A | * | 1/1994 | Jach et al. | 250/305 |
| 5,315,113 A | * | 5/1994 | Larson et al. | 250/305 |
| 5,543,648 A | | 8/1996 | Miyawaki | |
| 5,990,476 A | | 11/1999 | Larson et al. | |
| 6,447,891 B1 | | 9/2002 | Veerasamy et al. | |
| 2002/0102749 A1 | * | 8/2002 | Fielden et al. | 438/14 |
| 2003/0080291 A1 | * | 5/2003 | Larson et al. | 250/306 |
| 2003/0080292 A1 | | 5/2003 | Watson et al. | |

FOREIGN PATENT DOCUMENTS

| | | |
|---|---|---|
| EP | 0 590 308 | 4/1994 |
| EP | 0 594 394 | 4/1994 |

OTHER PUBLICATIONS

U.S. patent application 10/330,317 to Larson et al. filed Dec. 27, 2002.*

"Amicus: A High Speed Etching Source—Development and Application," [online]. Presented at *AVS '99, the 46$^{th}$ International Symposium*, Seattle Wash., Oct. 26, 2001, [retrieved on Oct. 11, 2001]. Retrieved from the Internet: <URL:http://www.kratos.com/EApps/Kaufmn.html>. (5 pgs.).

Briggs et al., eds., *Practical Surface Anlysis 2$^{nd\ Ed.}$*, vol. 1, "Auger and X–ray Photoelectron Spectroscopy," Sec 5.4.2, John Wiley & Sons, Ltd., Chichester 1995; cover page, title page and 244–248. (6 pgs.)

Gardner et al., "Surface Characterization of Carbon Fibers Using Angle–Resolved XPS and ISS," *Carbon*, 1995;33(5):587–595.

Gibson et al., "Characterizing Nanometer Oxy–nitride Films with ESCA Low Energy Sputter Depth Profiles," Presented at 15$^{th}$ International Vacuum Congress (IVC–15), AVS 48$^{th}$ International Symposium (AVS–48), 11$^{th}$ International Conference on Solid Surfaces (ICSS–11), Oct. 28, 2001. Abst. (1 pg.)

(List continued on next page.)

*Primary Examiner*—Nikita Wells
*Assistant Examiner*—Christopher M. Kalivoda
(74) *Attorney, Agent, or Firm*—Blakely, Sokoloff, Taylor & Zafman

(57) ABSTRACT

The present invention provides for characterization of a film (e.g., thickness determination for a silicon oxynitride film) using a comparison process (e.g., a fitting process) to compare measured peak shapes for elemental and/or chemical species (e.g., Si peak shapes previously measured for a particular process to be monitored) to collected spectral data (e.g., using a non-linear least squares fitting algorithm).

55 Claims, 17 Drawing Sheets

OTHER PUBLICATIONS

Hufner et al., "Core–line asymmetries in the x–ray–photoemission spectra of metals," *Phys. Rev. B.*, 1975;11(2):678–683.

Kilo et al., "Reaction Induced Surface Segregation in Amorphous CuZr, NiZr and PdZr Alloys—an XPS and SIMS Depth Profiling Study," *Journal of Alloys and Compounds*, 1996;236:137–150.

Moulder et al., "Ultra Shallow Depth Profiling by ESCA and SIMS," Presentation at National Symposium of American Vacuum Society (AVS), Baltimore, MD, Nov. 2–6, 1998, 31 pgs.

Oswald et al., "XPS Depth Profile Analysis of a Thin Non–Conducting Titanate Superlattice," *Mikrochim. Acta*, 2000; 133:303–306.

Otte et al., "XPS and Raman Investigations of Nitrogen Ion Etching For Depth Profiling of $CuInSe_2$" and $CuGaSe_2$ *Thin Solid Films*, 2000;361–362:498–503.

"PHI Quantum 2000 Scanning ESCA Microprobe™," Product Information. Physical Electronics, Inc., 1999; 8 pgs.

Principe et al., "Pushing The Limits of Nitrogen Doped Silicon Oxide Gate Dielectric Materials: The Material Characterization Role of TEM/STEM, PEELS, and XPS," Presented at American Vacuum Society 48th International Symposium, San Francisco, CA, 2001, Oct. 28–Nov. 25th Abst. (24 pgs.)

Shirley, "High–resolution x–ray photoemission spectrum of the valence bands of gold," *Phys. Rev. B.*, 1972;5(12):4709–4714.

* cited by examiner

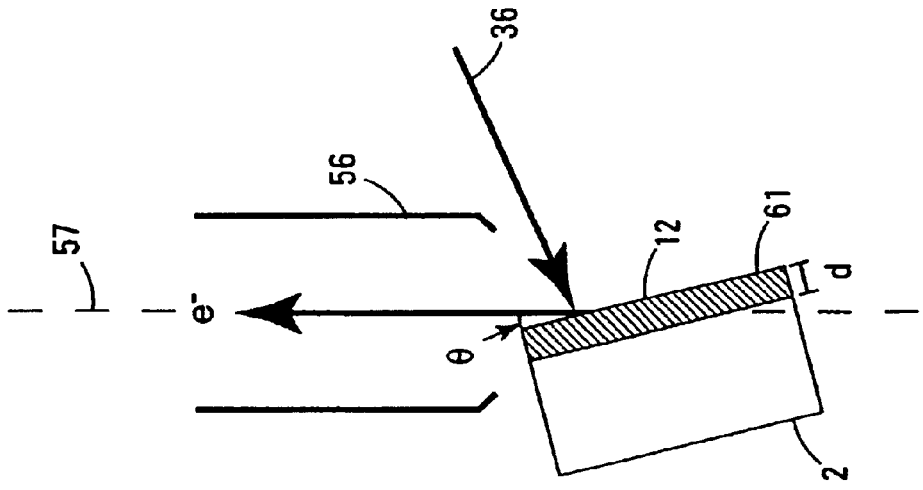
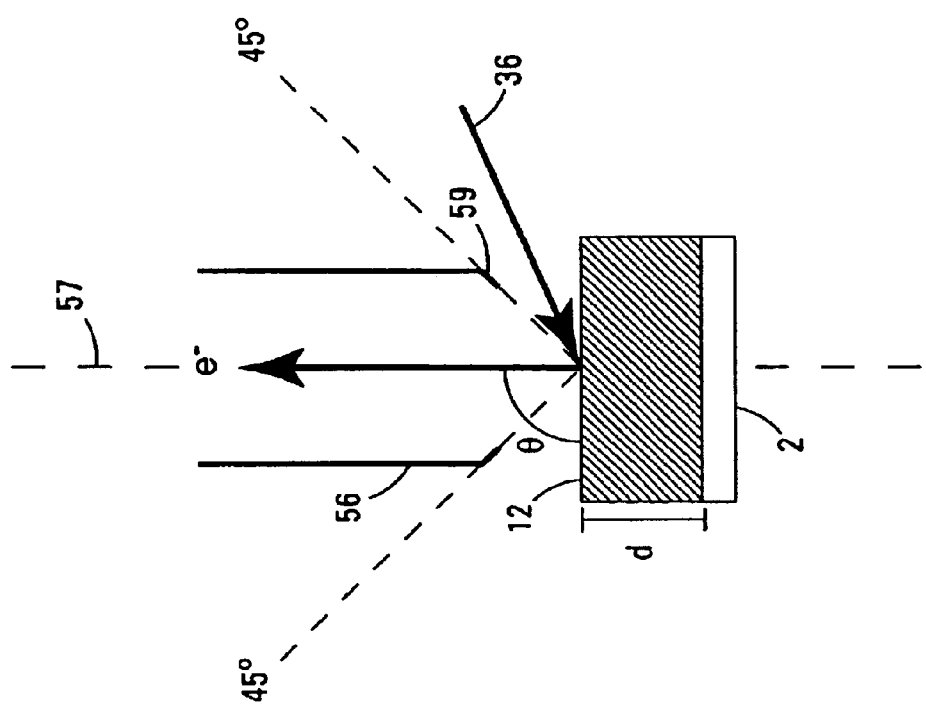

NONDESTRUCTIVE CHARACTERIZATION OF THIN FILMS USING MEASURED BASIS SPECTRA

FIELD OF THE INVENTION

The present invention relates to the characterization of solid samples, e.g., thin films. More particularly, the present invention pertains to the use of nondestructive techniques to characterize such samples.

BACKGROUND OF THE INVENTION

Characterization or analysis of samples (e.g., thickness of a thin film, elemental and/or chemical species concentration in a thin film formed on a substrate, etc.) is necessary in the manufacture of many different types of devices (e.g., electronic and optical electronic devices). For example, it may be necessary to determine the composition of thin dielectric films (e.g., gate oxide films, tantalum nitride films, etc.) formed in known semiconductor integrated circuit devices, such as processing devices and memory devices. Increases in the density of such devices on an integrated circuit chip and reduction in device dimensions require the advancement of production processes and characterization technologies related to the materials used to fabricate such devices.

For example, recent developments in the fabrication of semiconductor devices may employ shallow implant and/or other ultra-thin structures. In one particular example, gate oxide layers have become very thin films, typically in the range of about 1 to 10 nanometers in thickness. Such thin films are difficult to characterize. Such structures will require characterization techniques that have improved sensitivity over conventional characterization techniques.

Further, such techniques may also require the characterization to be performed with ample speed. For example, when such characterization techniques are used to monitor manufacturing tools or processes, e.g., metrology for wafer level manufacture of various films on substrates, the characterization must be done at suitable process speeds. Further, in monitoring of the manufacturing process, preferably, it is desired that such characterization be performed in a nondestructive manner, e.g., using a noninvasive process.

In addition to performing such process monitoring characterization of thin films noninvasively and with ample speed, one must be able to carry out such characterization techniques with precision on a consistent basis. In other words, measurements made or parameters determined using the characterization process must be repeatable with a suitable measurement precision (e.g., relative standard deviation, RSD). In such a manner, a process excursion, e.g., a process not performing as it is intended which typically results in product being produced that is not acceptable, can be detected.

Various techniques have been used for characterization of materials, e.g., to provide thickness measurements and/or to determine the concentration of trace and/or major components in such materials. For example, several of such methods include ellipsometry methods, transmission electron microscopy (TEM), scanning transmission electron microscopy (STEM), secondary ion mass spectrometry (SIMS), x-ray photoelectron spectrometry (XPS) (also known as electron spectroscopy for chemical analysis (ESCA)), Auger electron spectrometry (AES), and other electron beam methods.

Many of such techniques are sensitive to the near-surface region of a material. Further, many of these techniques also permit a measurement of material properties as a function of depth beneath the surface through depth profiling. In typical depth profiling, for example, continuous or periodic ion beam sputtering removes material from the surface of a sample to expose progressively deeper material at one or more various depths of the sample for further measurement and/or analysis. Generally known sputter rates may be used to determine the depth at which the surface measurements are completed. As such, a characterization of the sample as a function of depth beneath the surface can be attained. However, in process monitoring, such depth profiling techniques are in many circumstances inadequate. For example, depth profiling is an invasive and destructive process, and further, such processes generally take a relatively long period of time to complete, e.g., as compared to just surface measurements.

Further, even if such techniques are not used in a destructive depth profiling fashion, they are typically inadequate in many other respects with regard to characterization of various types of samples. This is particularly the case with respect to characterization of thin films, e.g., thin gate oxide films.

Optically based ellipsometry methods have been the standard method for monitoring $SiO_2$ gate films. However, the change in gate materials, from for example, $SiO_2$ to $SiO_xN_y$, has made a major impact on the usefulness of optical measurement tools. The index of refraction changes when nitrogen is added to the film. Since nitrogen content varies with depth, the index of refraction of the films is a variable making it difficult to use standard optical methods to monitor SiON films. In addition, the trend to thinner films (e.g., 18 angstroms, 12 angstroms, 8 angstroms . . . ) is challenging the fundamental limits of optical methods. The combination of these two effects has reduced measurement precision for thickness using such techniques rendering them ineffective for monitoring thickness and composition. Currently, for example, optical techniques achieve precision of 0.4% RSD for thin (e.g., less than 20 angstroms) un-nitrided oxide (e.g., $SiO_2$) films and 1.5–10% RSD for nitrided (e.g., SiON) oxide films.

TEM or STEM combined with electron energy loss spectroscopy (EELS) measurements can also provide thickness and some composition information. However, there are a number of issues that make the TEM impractical for use in production monitoring. For example, thickness measurement precision is typically greater than 2 angstroms and the cost of the needed equipment is generally prohibitive. Further, the length of time needed to perform such measurements is long (e.g., four hours per measurement) and a highly skilled specialist to prepare the sample and perform the measurements is typically a requirement.

Further, for example, SIMS, which has a very small sampling depth, is routinely used to quantify low level dopants and impurities in thin films (e.g., thin films less than 10 nanometers) because of this technique's extreme surface sensitivity (e.g., single atom layer sensitivity and ppm-ppb detection limits). However, sensitivity factors used for SIMS quantification are matrix dependent and accurate quantification requires the use of calibrated reference samples. For example, when the concentration of a dopant exceeds 1%, it becomes a significant part of the matrix further complicating the task of quantification. To monitor silicon oxynitride gate films via SIMS, it would be required to regularly (e.g., at least daily) analyze reference silicon oxynitride films with thickness and nitrogen dose certified by an external direct measurement technique such as XPS.

Further, AES has also been used for thin film characterization. However, the high intensity electron beam used to make Auger measurements can alter the apparent composition of a thin film by causing chemical damage (e.g., can damage $SiO_2$ films) or causing the migration of elements within the thin film. For example, there are concerns over the possible mobility of nitrogen within a film under the influence of an electron beam (e.g., nitrogen is known to migrate to the interface of an oxide-nitride stack (ONO) provided on silicon).

XPS, or ESCA, has been previously used to characterize thin films (e.g., ultra thin films less than 5 nanometers) such as lubricant coatings on computer hard disks with a measurement precision of 5% RSD. Further, characterization of other types of films such as SiON via XPS using standard practices has resulted in measurement precisions of 0.5% to 1.0%. For example, such standard practices involve the collection of data at relatively low analyzer angles such that depth resolution is enhanced. Such a low analyzer angle is typically less than 20 degrees. Use of a low analyzer angle generally results in a slow characterization process and also may result in problems associated with placement of the analyzer of the characterization system relative to the sample being analyzed. Yet further, existing data reduction methods which operate on the XPS collected data employ software tools for background subtraction and peak fitting that require frequent operator input making the results operator dependent and less precise.

In general, many of the techniques described above for characterizing thin films are invasive techniques, e.g., they involve destruction of at least one or more portions of the sample. Such techniques, e.g., those that use removal of material during depth profiling, are sufficient in many circumstances, e.g., research and development, product testing, etc., but do not provide for the ability to quickly analyze a thin film such as is necessary in production processes. For example, in such production processes, a thin film being formed typically needs to be analyzed so that such information can be used for production control, product test, etc., without loss of product due to invasive characterization of such films.

Nitrogen doped or nitrided silicon oxide is one material that is used as a gate oxide for a transistor structure. Such gate structures are only one of the growing number of semiconductor related material structures under development that require characterization at an unprecedented level of complexity. Such challenges are not limited to merely a desire for near-atomic and monolayer spatial resolution, but are magnified by the level of accuracy, precision and speed demanded by the semiconductor fabrication industry.

There is a distinct need to develop adequate characterization methods and systems. The ability to characterize materials at such levels is necessary to enable product development and also necessarily precedes evolution of process control. For example, there is a need for suitable systems and methods to provide parametric thickness, nitrogen dose, and nitrogen distribution information for thin nitrided silicon oxide films such as used for transistor gate oxides.

SUMMARY OF THE INVENTION

Systems and methods according to the present invention for characterizing samples are described herein. In particular, such systems and methods are particularly beneficial for the non-destructive analysis of thin films. As used herein, a thin film is generally defined as being less than about 10 nanometers in thickness. The present invention is also particularly beneficial for use with thin films having a thickness that is less than about 4 nanometers.

The present invention can provide, for example, an accurate measure of a component concentration (e.g., an elemental and/or a chemical species) in a thin film, thickness of such a thin film, distribution or uniformity of a component concentration across the thin film, and/or uniformity of thickness across such a thin film. Further, the present invention can detect process excursions based on the determination of thickness of a film and/or detect a process excursion by detecting a change in nitrogen concentration determined by measurement of nitrogen signal and correlation of that measurement with film thickness. Such change in nitrogen concentration may be due to either a change in total nitrogen in the film or a change in the nitrogen depth distribution.

The present invention may employ novel data reduction that includes, for example, a fitting process to compare measured peak shapes for elemental and/or chemical species (e.g., Si peak shapes previously measured for a particular process to be monitored) to collected XPS data, e.g., using a non-linear least squares fitting algorithm. Such fitting is performed without the necessary conventional operator input. In such a manner, e.g., with elimination of frequent operator input that conventionally made the results operator dependent and less precise, enhancement of the data quality yielding improved precision is accomplished.

A method for use in characterizing a film according to the present includes providing at least one measured spectral peak shape (i.e., measured basis spectra) representative of a concentration of at least one component of a film (e.g., a dielectric film such as a silicon oxynitride film and/or a film having a thickness of less than about 10 nanometers, and even less than about 4 nanometers), wherein the film is formed on a substrate by a particular process defined by a set of processing conditions. An acquired spectrum is provided for an additional film to be characterized, wherein the additional film is formed on a substrate by the particular process defined by the set of processing conditions. The at least one measured spectral peak shape is compared to the acquired spectrum and at least a thickness measurement is determined for the film to be characterized based on the comparison.

In one embodiment of the method, a spectral background is calculated for the acquired spectrum and the at least one measured spectral peak shape and the spectral background are compared to the acquired spectrum.

In yet another embodiment of the method, the at least one measured spectral peak shape includes a measured spectral peak shape representative of a concentration of the at least one component in the film and at least another measured spectral peak shape representative of a concentration of the at least one component in at least a portion of the substrate. Further, for example, the acquired spectrum may include overlapping peak areas representative of a concentration of the at least one component (e.g., silicon) in the additional film and the at least one component (e.g., silicon) in at least a portion of the substrate. In such a case, the comparison of the at least one measured spectral peak shape and the spectral background to the acquired spectrum may include fitting the acquired spectrum to the measured spectral peak shape representative of a concentration of the at least one component in the film and the at least another measured spectral peak shape representative of a concentration of the at least one component in at least a portion of the substrate using the spectral background calculated from the acquired spectrum to extract separate acquired spectrum peak areas from the overlapping peak areas. One of the separate acquired spectrum peak areas is representative of a concentration of the at least one component (e.g., silicon) in the additional film and the another separate acquired spectrum peak area is representative of the at least one component (e.g., silicon) in at least a portion of the substrate.

In another embodiment of the method, providing the at least one measured spectral peak shape may include providing a high resolution spectrum. After subtracting a spectral background from the high resolution spectrum, at least one narrow measured spectral peak shape representative of a concentration of at least one component of a film and at least another narrow measured spectral peak shape representative of a concentration of the at least one component in at least a portion of the substrate can be separated. A broadening function can then be applied to the at least one narrow measured spectral peak shape and the at least another narrow measured spectral peak shape to match a resolution of the acquired spectrum.

In another embodiment of the method, surface spectral measurements for use in the process are provided by irradiating the additional film with x-rays resulting in the escape of photoelectrons, detecting the escaping photoelectrons, and generating a signal representative of the detected photoelectrons. The surface spectral measurements are based on the generated signal. An analyzer may be provided that includes an input lens receptive of photoelectrons with the input lens having a central axis extending therethrough. The input lens is positioned such that the central axis of the input lens is at an analyzer angle relative to a surface of a film, wherein the analyzer angle is in the range of about 45 degrees to about 90 degrees, preferably, in the range of about 60 degrees to about 90 degrees. Further, for example, irradiating the additional film with x-rays may include irradiating the additional film with x-rays from a low energy x-ray source less than 2000 eV.

A system for use in characterizing a film is also described according to the present invention. The system includes an x-ray source operable to irradiate one or more films with x-rays resulting in the escape of photoelectrons and an analyzer operable to detect escaping photoelectrons. The analyzer is operable to generate a signal representative of the detected photoelectrons for use in providing an acquired spectrum for one or more films. Further, the system includes a computing apparatus operable to recognize at least one measured spectral peak shape representative of a concentration of at least one component of a film, wherein the film is formed on a substrate by a particular process defined by a set of processing conditions. The computing apparatus is further operable to recognize an acquired spectrum for an additional film to be characterized, wherein the additional film is formed on a substrate by the particular process defined by the set of processing conditions. The at least one measured spectral peak shape can be compared to the acquired spectrum for use in determining at least a thickness measurement based thereon.

In other embodiments of the system, the system is operable to implement one or more of the functional processes described above and also elsewhere herein. Further, a program storage media, readable by a media read apparatus under control of a computer, tangibly embodying a program executable to perform a process for characterization of thin films is also described. The program is also operable for implementation of one or more of the functional processes described above and also elsewhere herein.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

BRIEF DESCRIPTION OF THE DRAWINGS

FIGS. 7A and 7B are illustrative diagrams for use in describing analyzer angle embodiments according to the present invention.

DETAILED DESCRIPTION OF THE EMBODIMENTS

Figure 1:
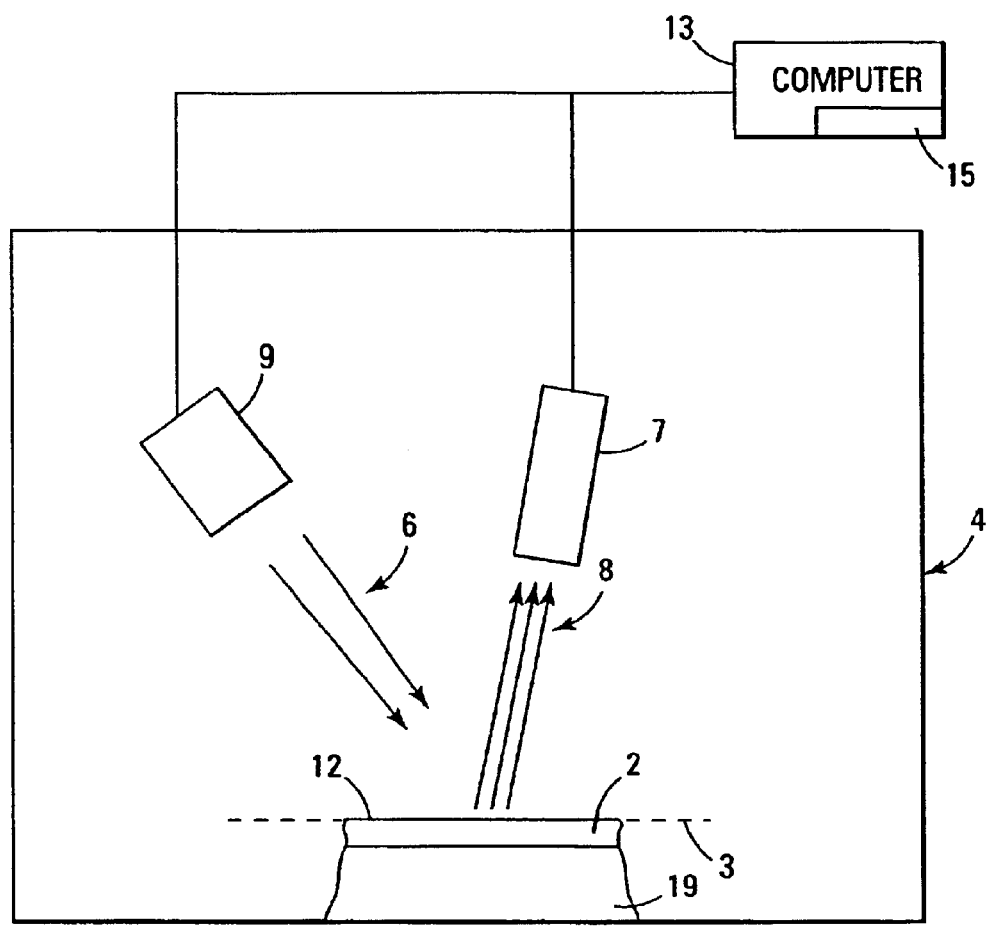
FIG. 1 is an illustrative diagram of an analysis system according to the present invention.

Analysis systems and methods according to the present invention shall be described with reference to FIGS. 1–15. Such systems and methods may be used to analyze complex materials in development processes, assist to identify solutions for processing problems, identify contamination sources, improve yields in the fabrication of devices, assist in monitoring processing and manufacturing devices, and be used in failure analysis techniques. Further, the systems and methods may be used in the characterization of thin films relating to various industrial applications, such as semiconductor devices, magnetic storage media, display technology, automotive materials, aerospace materials, polymer products, and/or biomaterials.

Generally, the analysis systems and methods described herein preferably provide non-destructive, e.g., non-invasive, analysis systems and methods that generally include the collection of surface spectral measurements (e.g., XPS spectra) from a thin film. Thereafter, a characteristic of the thin film formed by a particular process defined by a set of processing conditions, e.g., thickness of a thin nitrided silicon oxide film, nitrogen concentration in the thin nitrided silicon oxide film, etc., can be determined based on the surface spectral measurements with use of effective data processing methods as further described herein.

Generally, for example, with regard to nitrided oxide films, e.g., silicon oxynitride films, the present invention involves systems and methods for the non-destructive measurement of the thickness and nitrogen content of such films, e.g., silicon oxynitride transistor gate dielectric films that have a thickness of less than 4 nanometers. With use of such a non-destructive measurement, excursions from desired manufacturing process conditions (e.g., tool conditions) can be detected. In other words, a process or process tool that is not performing as it should be may be detected. For example, if the present invention provides measurement of thickness and/or nitrogen content that are outside of predefined acceptable statistical deviations for the resultant film formed by the process, a manufacturing process excursion may be detected. Notification to the user of such an excursion may be provided by any sort of alerting mechanism, e.g., alarm, flashing of data on a screen, or any other indicator techniques.

The present invention provides the ability to confirm the thickness of at least certain films, such as nitrided oxide films, to a precision of ±0.2% RSD and also to confirm nitrogen content of a silicon oxynitride film to within ±0.5% RSD. Further, the present invention provides improved tool-to-tool matching capabilities. In other words, with regard to tool-to-tool matching, such precision is maintained whether measurements are taken on a single particular instrument or whether they are performed on different instruments of the same type.

Further, with reference to a silicon oxynitride film (which as used herein represents any film formed of silicon, oxygen, and nitrogen), at least in one embodiment, the present invention performs surface spectral measurements to provide the Si2p region (i.e., $Si^0/Si^{4+}$) of the XPS spectra following the growth of a silicon oxynitride gate dielectric film on a silicon substrate using a low energy x-ray source and a high analyzer angle, as shall be described further below. Using the methods according to the present invention, the thickness of the silicon oxynitride gate film can be calculated using the Si2p spectrum and the automated measurement software according to the present invention developed to perform the film thickness measurement with high precision. Further, the concentration of nitrogen in the silicon oxynitride film can be calculated using the Si2p and nitrogen N1s spectra and the automated measurement software, as further described herein, which is able to perform surface XPS dose calculations with high precision. In addition, for example, film uniformity may be determined by repeating the thickness and/or dose measurements at multiple locations on a wafer on which the silicon oxynitride film is deposited.

The present invention deviates from established standard practices for instrument conditions and data reduction methods. For example, the XPS spectra utilized are preferably collected according to the present invention with the instrument conditions optimized for elemental sensitivity at the expense of energy resolution and surface sensitivity, e.g., high analyzer angle.

Further, as described in the Background section herein, existing data reduction methods employ software tools for spectral background subtraction and peak fitting that require frequent operator input, making the results operator-dependent and less precise. The present invention uses methods that do not require such operator input. For example, in one embodiment of the present invention, the correct spectral background is mathematically determined and the spectral background is fit with measured, e.g., not theoretical, XPS peak shapes for components of the thin film being characterized using, for example, a non-linear least squares fitting algorithm. In such a manner, operator input is eliminated and the fitting algorithm enhances the data quality yielding a precision of less than 0.2% RSD for film thickness and 0.5% RSD for concentration dose (e.g., nitrogen dose in a silicon oxynitride film).

In another embodiment of the present invention, the acquired spectrum for the film to be characterized is used by itself, without a fitting algorithm, to provide desired information (e.g., thickness) characterizing the film.

The present invention exploits the fact that film thickness can be measured with high precision using XPS surface measurements and effective data processing methods. Further, observation of and exploitation of the fact that for a given film growth process, for example, when characterizing a silicon oxynitride film, the surface nitrogen concentration correlates with the total N dose incorporated during film growth. Such XPS surface measurements of N concentration can be made in a few seconds and converted to dose according to the present invention. This is possible because the silicon oxynitride gate films are very thin and the XPS surface measurement volume extends through the film and into the silicon wafer below the film. According to the present invention, nitrogen dose can be measured with high precision using such XPS surface measurements.

As such, at least with respect to silicon oxynitride films, a single, non-destructive XPS measurement can provide both film thickness and nitrogen dose. High measurement precision (i.e., less than 0.2% RSD for film thickness and less than 0.5% RSD for nitrogen dose) can be attained. Yet further, the sensitivity of the present invention to small changes in processing conditions is effectively achieved.

Figure 2:
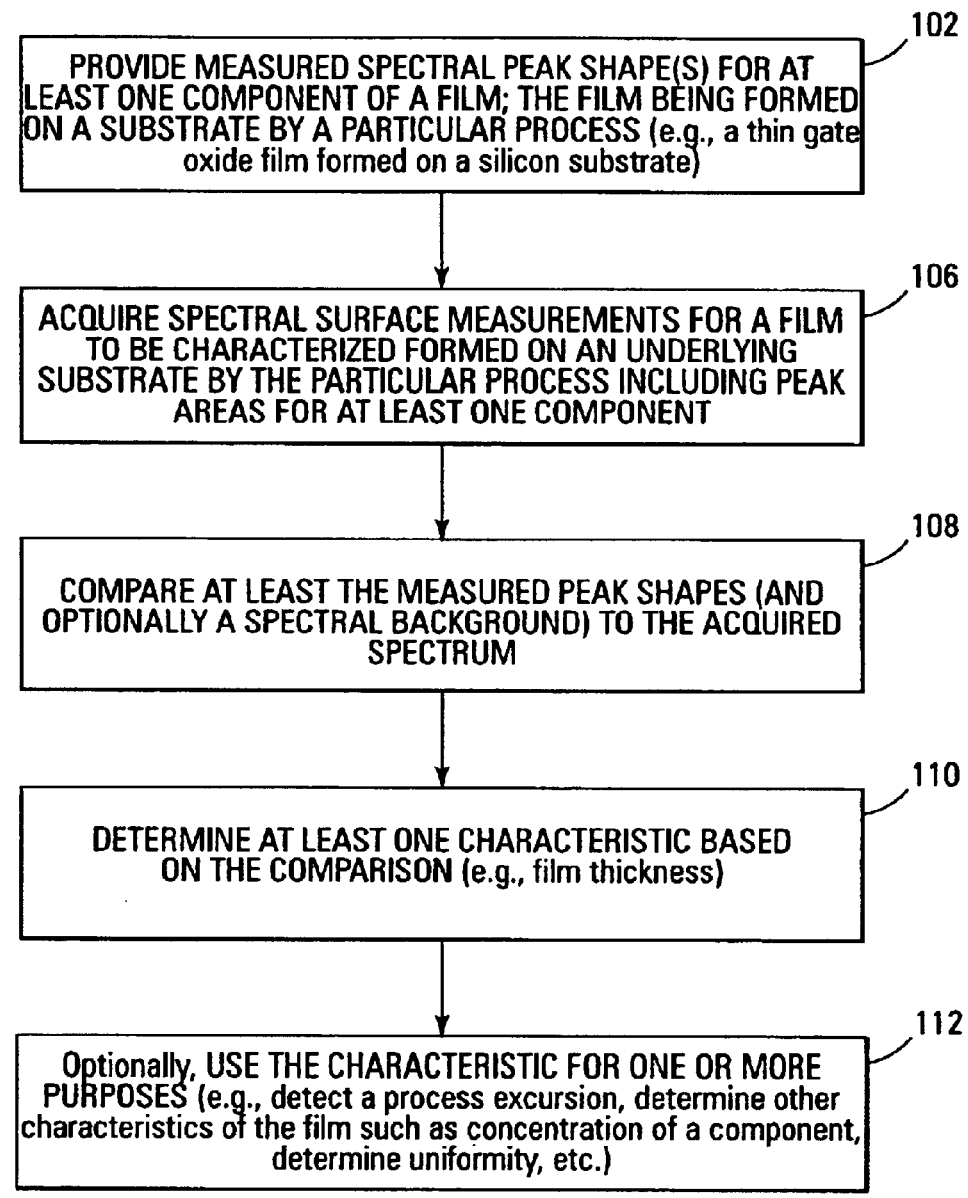
FIG. 2 is an exemplary diagram of a film characterization method that may be carried out by the illustrative analysis system shown in FIG. 1.
Figure 8A:
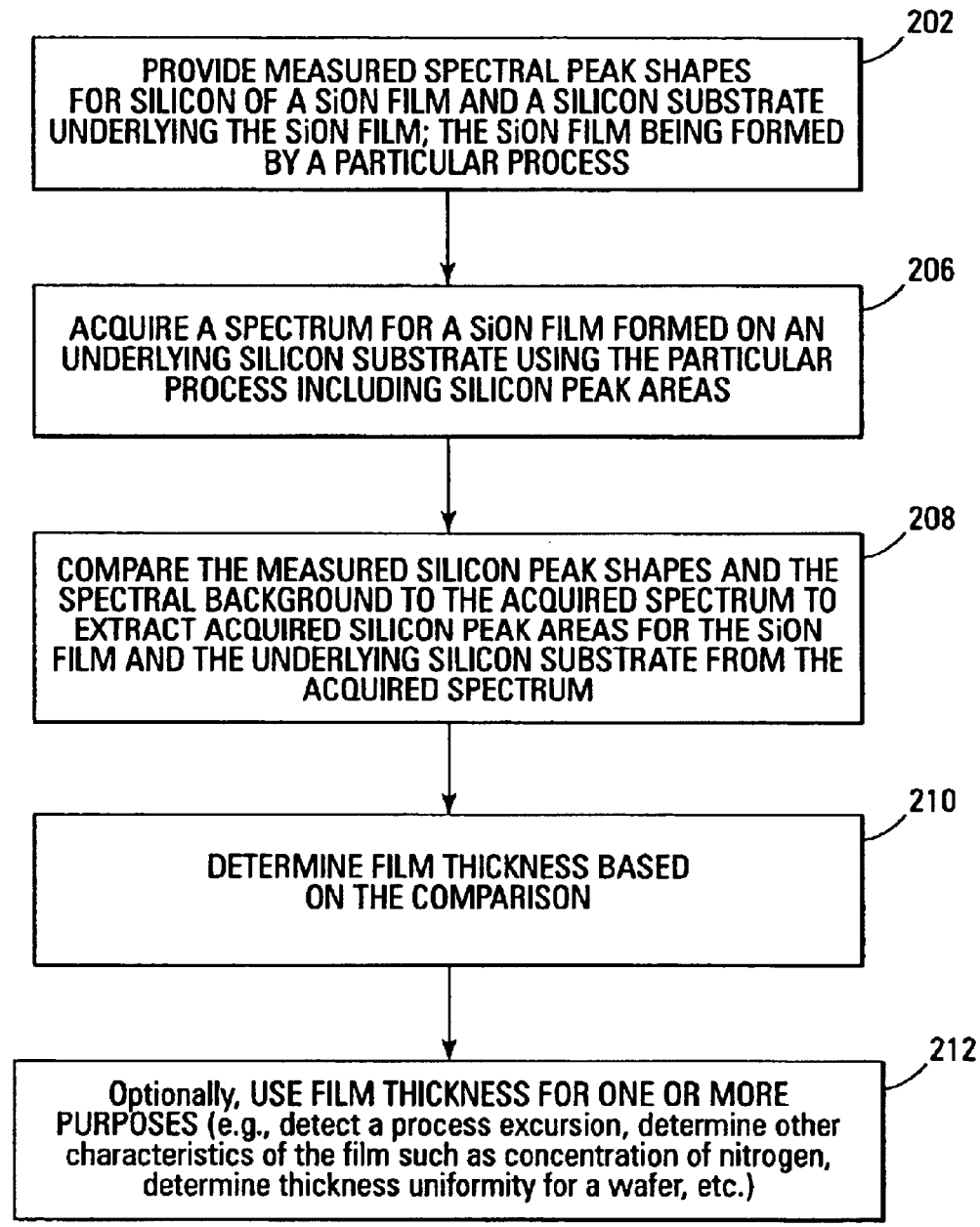
FIG. 8A is an illustrative flow diagram of one embodiment of a thin dielectric film characterization method for use in determining thickness of a film according to the present invention.

FIG. 1 generally shows one embodiment of an illustrative analysis system 1 operable for use in characterizing a film 2 having a sample surface 12 positioned at an analysis plane 3 of an analysis instrument 4; the film 2 having been formed on a substrate 19. Coupled to the analysis instrument 4 is a computer apparatus 13 operable under control of one or more programs 15 to carry out one or more various characterization processes, e.g., film characterization method 100 as shown in FIG. 2, thin dielectric film characterization method 200 as shown in FIG. 8A used to calculate thickness, as well as, for example, other methods such as those illustrated in FIGS. 3–4, 9, 11–12, and 14.

The film 2 having the film surface 12 may be formed of any one or more components. The term component is defined herein as one or more elements and/or chemical species. For example, such components may include elements and/or chemical species composing materials used in semiconductor fabrication, magnetic storage media, or any of the other various applications described above. In other words, for example, in the context of semiconductor fabrication the film may include layers formed of oxygen, silicon, carbon, fluorine, silicon dioxide, nitrogen, etc.

Preferably, the present invention is useful in the characterization of thin films, particularly thin dielectric or insulating films. As used herein, a thin film refers to a film or layer having a thickness of less than about 10 nanometers. However, the present invention may be beneficial in characterizing films as thick as 100 nanometers and is particularly beneficial for analyzing films having a thickness of less than 4 nanometers.

Further, the present invention is particularly advantageous in characterization of certain oxide layers. For example, such oxide layers may include silicon oxide layers, silicon oxynitride films, nitrided oxide layers, etc. For example, such oxide layers may be formed as thin films having thicknesses less than about 10 nanometers, and even less than 4 nanometers, and used for gate oxides in the fabrication of semiconductor devices such as field effect transistors (FET). Such transistors are used in various integrated circuit devices including processing devices, memory devices, etc.

Although the present invention is described in preferred embodiments herein with respect to the characterization of, for example, silicon oxide and silicon oxynitride films, the present invention may also be useful for characterizing other thin dielectric films, such as those with dopants other than nitrogen. For example, the present invention may be useful in characterizing thin dielectric films such as transition metal oxides and tantalum nitride. In other words, one skilled in the art will recognize that the present invention is not limited to any particular thin film, such as silicon oxynitride, but may be effective for characterizing other thin films as well.

Further, in various embodiments herein, silicon oxynitride is characterized using the present invention. However, in many instances, a starting film (i.e., a precursor film) of silicon oxide is used and then later nitrided to form a silicon oxynitride film. The present invention may be effective to measure the precursor silicon oxide film thickness as well as the later grown silicon oxynitride film. This may be particularly beneficial in process control since the final silicon oxynitride film thickness is partially dependent on the precursor silicon dioxide film thickness.

As one skilled in the art will recognize from the description above, the film may take one of many different forms. For example, the film may be a layer formed on a substrate or a region formed within a substrate, as well as any other film or stack of layers formed of a material that would benefit from being characterized according to the present invention. In other words, the term film as used herein refers to both a single film or film formed of multiple layers (e.g., a stack of layers).

Further, the term substrate as used herein is representative of almost any object upon which material may be formed or in which material may be formed, and the present invention is not to be taken as limited to any particular material or structure listed herein. However, the present invention does have particular advantages in characterizing certain thin films, e.g., gate dielectric layers such as gate oxide layers, formed on a silicon substrate.

As used herein, characterization refers to the determination of one or more characteristics of the film being analyzed. For example, characterization may refer to the determination of concentration of components in a film, the distribution of such components, or the determination of one or more other physical or chemical characteristics of the film, e.g., thickness, bonding states, elemental and chemical composition in the regions, etc. The present invention is particularly beneficial in the determination of thickness and concentration of components (e.g., elements and/or chemical species) in thin films.

Preferably, computer apparatus 13 includes a computing system operable to execute software 15 to provide for the characterization of films according to the present invention. Although the computer apparatus 13 may be implemented using software 15, executable using a processor apparatus, other specialized hardware may also be used to provide certain functionality required to provide a user with characterization of a film. As such, the term computer apparatus 13 as described herein includes any specialized hardware in addition to processor apparatus capable of executing various software routines.

The computer apparatus 13 may be, for example, any fixed or mobile computer system, e.g., a personal computer, and/or any other specialized computing unit provided as a functional part of or as a supplement to an analysis instrument used according to the present invention. The exact configuration of the computer system is not limiting and most any device capable of providing suitable computing capabilities and/or control capabilities may be used according to the present invention. Further, various peripheral devices, such as a computer display, a mouse, a keyboard, a printer, etc., are contemplated to be used in combination with a processor in the computer apparatus 13. For example, a computer display or printer may be used to print or display various types of information, e.g., peak shapes and areas showing concentration of components (e.g., elements and/or chemical species) of the film, distributions of components of a film across a wafer on which it is formed, spectra of the components, etc.

Figure 5:
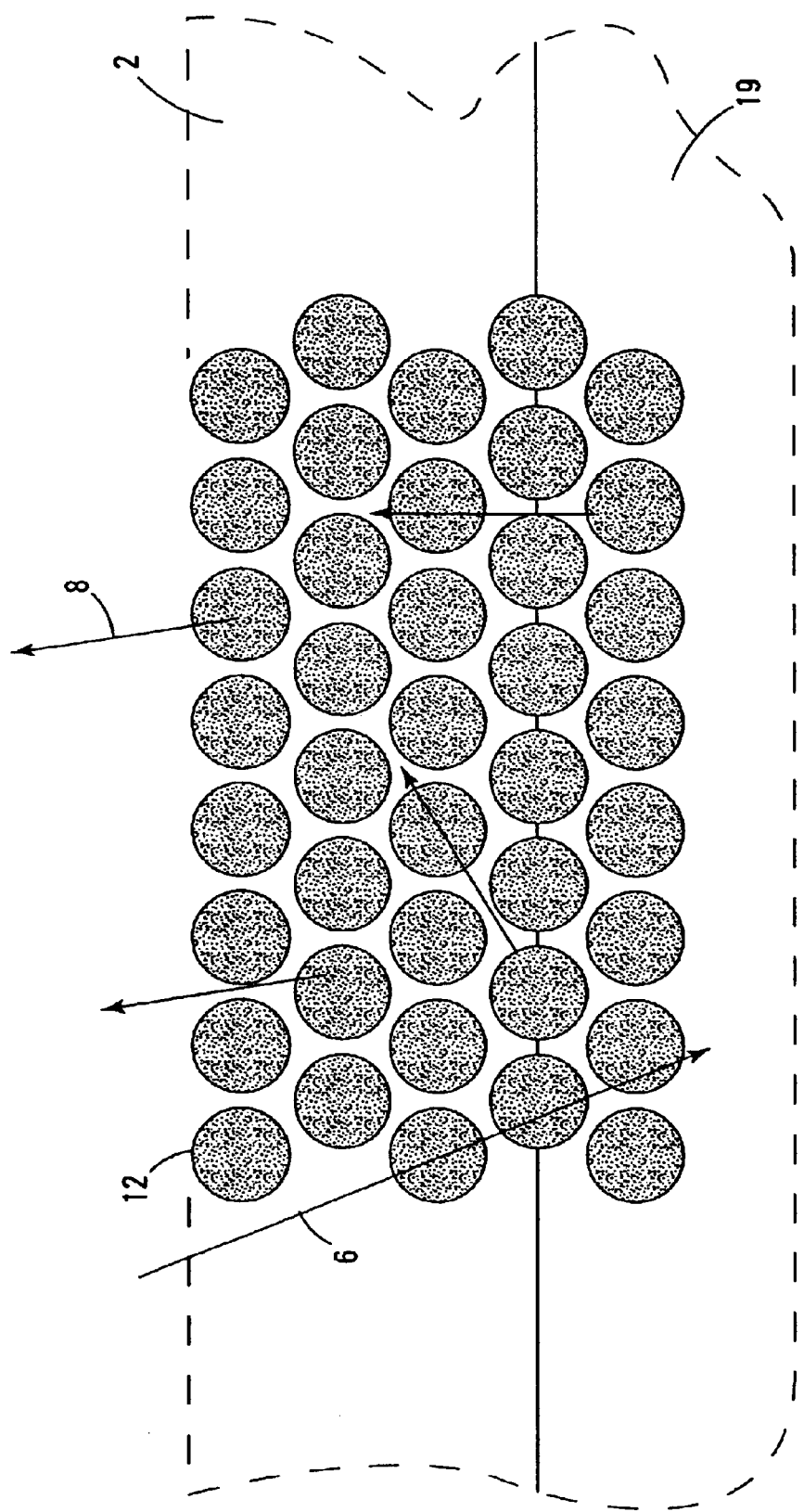
FIG. 5 is a diagram showing the surface sensitivity of a thin film being irradiated with x-rays for use in illustrating the present invention.

The analysis instrument 4 of the analysis system 1 may be any instrument that provides spectral data that can be analyzed using the data processing techniques described herein. Preferably, according to the present invention, the analysis instrument 4 of the analysis system 1 includes an x-ray source 9 operable to irradiate the film 2 with x-rays 6 resulting in the escape of photoelectrons from an analysis volume including a portion of the film 2 and a substrate portion therebelow. As shown in FIG. 5, the x-rays 6 penetrate deep into the film surface 12, exciting photoelectrons 8 to escape from the film 2 and also, most likely, from at least a region of the substrate 19 upon which the film 2 is formed depending on the thickness of the film 2. However, photoelectrons can travel only a short distance before their energy is modified due to interaction with neighboring atoms. Only photoelectrons that escape at their original energy contribute to a peak in a spectrum used for the analysis of the film. Depending on the escape depth of the constituents of the sample volume, the average depth of analysis for a surface irradiated by x-rays 6 is in the range of about 10 angstroms to about 50 angstroms depending upon the sample material. The photoelectron energies generally include a low energy peak in the range of up to 10 eV, usually about 2 eV to 5 eV, plus higher kinetic energy peaks or lines characteristic of elemental and/or chemical species in the irradiated analysis volume.

An analyzer 7 of the analysis system 1 is operable to detect photoelectrons 8 escaping from, for example, the film 2 and underlying substrate. The analyzer 7 is positioned at an analyzer angle (as further described below) relative to the analysis plane 3 or, in other words, relative to the film surface 12 which is preferably in the analysis plane. The analyzer 7 is used to detect photoelectrons for generation of a signal representative thereof to be used for the characterization of the film 2. Signals from the analyzer corresponding to intensity of detected photoelectrons are provided to the computer apparatus which operates on the signals to provide photoelectron energy information and thereby surface spectra measurements of components that are present in the analyzed volume, e.g., the film irradiated and a portion of the underlying substrate.

The analysis system 1 diagrammatically shown in FIG. 1 is operable to perform surface spectra measurements for use in the characterization processes described herein. Upon the collection of surface spectra measurements, film characterization may be performed according to the exemplary method 100 as described with reference to FIG. 2 or the exemplary method 300 described with reference to FIG. 3. For example, the film characterization methods 100, 300 may be used to provide thickness measurements for the film, dose concentration calculations, etc.

In the characterization of films, particularly thin films or layers, conventional XPS techniques have been used to acquire surface spectra measurements. Generally, depth resolution is enhanced with the use of lower analyzer take-off angles detecting photoelectrons escaping from the surface at a low take-off angle, e.g., much less than 40 degrees relative to the film surface, preferably about 10 degrees to about 20 degrees. However, as described further below, such lower analyzer angle restricts the size of the samples which can be characterized, results in a lower sensitivity, and also results in slower capture of surface measurement data, e.g., lower analyzer angles require more time, relative to the higher analyzer angles to capture sufficient signal for generation of surface spectra measurements used in the characterization of films. Such slow capture of surface measurement data is undesirable according to the present invention where speed is of particular importance, particularly when detecting process excursions on a manufacturing line.

To improve the characterization of such thin films, analysis system 1 (e.g., an XPS or ESCA system) is configured with one or more particular features and/or is operated under one or more particular parameters so as to eliminate problems associated with the conventional methods. Such configurations and/or parameters are described further below with reference to one or more embodiments shown in the illustrative figures. One skilled in the art will recognize that one or more of such parameters and/or features of the analysis system 1 as further described below may be used in combination with other features or may be used alone to enhance the characterization of the film 2 according to the present invention.

The present invention may be employed by using any x-ray photoelectron spectroscopy analysis system (e.g., those distributed under the trade designations PHI 5800, PHI Quantum 2000 Scanning ESCA Microprobe™ and PHI Quantera Scanning XPS Microprobe™ available from Physical Electronics, Inc. (Eden Prairie, Minn.)). The systems may be modified and/or operated at one or more of the parameters described herein to provide for thin film analysis.

Figure 6:
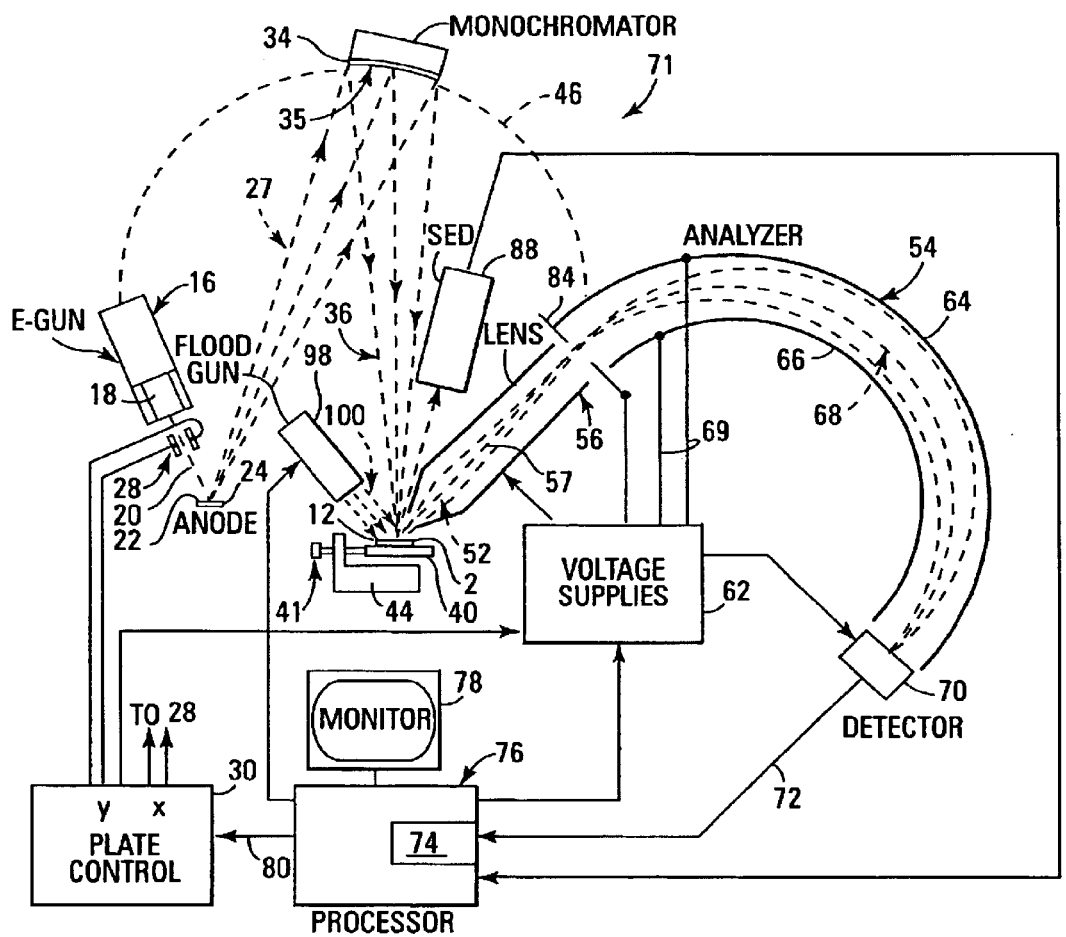
FIG. 6 is a schematic diagram of one illustrative embodiment of a portion of the system shown in FIG. 1.

FIG. 6 shows in more detail one illustrative embodiment of portions of an analysis system 1 operable for carrying out the characterization according to the present invention. The analysis instrument 71 shown in FIG. 6 for analysis of a film 2 provides a more detailed illustrative embodiment of the x-ray source 9, the analyzer 7, and the computer apparatus 13 shown generally in FIG. 1. FIG. 6 was previously described in U.S. Pat. No. 5,315,113 to Larson et al., issued 24 May 1994, and entitled "Scanning and High Resolution X-ray Photoelectron Spectroscopy and Imaging." The detailed diagram of FIG. 6 is but one illustrative embodiment of an x-ray source and an analyzer that may be used according to the present invention and is not to be construed as limiting the present invention to any particular components shown therein.

The instrument 71 of FIG. 6 includes an electron gun 16 having an appropriate electron lens system 18 for focusing the electron beam 20 onto the surface 22 of a target anode 24. The electron gun 16 may be a conventional type, modified to optimize for higher power and larger beam size. The gun beam 20 is focused to a selected spot on the anode surface 22. The spot is preferably as small as practical, e.g., down to about 4 microns. The focusing of the beam 20 onto the spot of the anode surface results in the generation of x-rays 27 from the anode 24 and, in particular, from the selected anode spot. The electron gun may be any suitable gun such as one operable at 20 kV over 1 watt to 60 watts with a selectable beam size of 4 microns to 200 microns, such as described in U.S. Pat. No. 5,315,113.

The target anode 24 may be formed of any metal such as aluminum that provides a desired x-ray emission energy band. For example, the band is generally substantially a line of small energy width. Preferably, the target anode is at or near ground potential, and the gun cathode is operated at a negative voltage, for example, −20 kV, with respect to the anode to effect generation of x-rays including the desired-band of x-rays of predetermined energy. In one preferred embodiment, the selected energy band is the aluminum K-alpha line at 1.4866 keV.

Although a monochromatic Al Kα x-ray source is used in the above exemplary embodiment of analysis instrument 71, it may be advantageous from a cost and measurement speed perspective to use other x-ray sources. For example, a non-monochromatic x-ray source such as Mg or Al Kα x-ray sources may provide additional speed in collecting surface spectra measurements.

Deflection plates 28 selectively direct or aim the electron beam 20 from the electron gun 16 to the spot on the anode 24 which is selected out of an array of such spots on the anode surface 22. Voltages from a deflection plate control 30, controlled by a processor 76 via line 80, are applied to the deflector plates, which are arranged in both x and y axes, to establish the amount of deflection of the beam, and thereby the selected position of the spot. The spot may be held stationary. Alternatively, the control 30 may provide rastering of the focused electron beam 20 across the flat surface of the anode, e.g., over the array of anode spots across the anode surface, and-the x-rays 27 are emitted sequentially from successive anode spots. For example, raster speed may be 100 Hz in the dispersive direction and 10 kHz in the non-dispersive direction.

A Bragg crystal monochromator 34, advantageously single-crystal quartz, is disposed to receive a portion of the x-rays 27 from the anode 24. The monochromator has a crystallographic orientation and a concave configuration 35 to select and focus a beam of x-rays 36 in the desired energy band, e.g., the K-alpha line, as an x-ray spot on the film surface 12 to be analyzed. The x-ray spot is an image of the anode spot on the film surface 12. Alternatively, rastering of the x-ray spot may be used to cover a desired area of the sample surface. The film 2 rests on a stage 40 advantageously having orthogonal micrometer positioners 41 for manual or motorized positioning with respect to a support 44 in the instrument. The film 2 may be moved to provide coverage over an even larger surface area.

Although a Bragg crystal monochromator is preferred, other focusing apparatus may be suitable. Such focusing apparatus may include grazing incidence mirrors, Fresnel zone plates, and synthetic multilayer devices of alternating high and low density material (e.g., tungsten and carbon). In each case, the reflector is curved to focus the diffracted x-rays onto the specimen.

A suitable arrangement of components for the analysis instrument 71 is based on the conventional Rowland circle 46. In this arrangement, the anode surface 22, the crystal 34, and the film surface 12 are substantially on the circle, for example, as taught in U.S. Pat. No. 3,772,522, to Hammond et al., issued 13 Nov. 1973 and entitled "Crystal Monochromator and Method of Fabricating a Diffraction Crystal Employed Therein."

The x-rays 36 cause photoelectrons 52 to be emitted from the selected active pixel area of an analysis volume, e.g., the film 2 and portion of underlying substrate. The electron energies generally include a low energy peak in the range of up to 10 eV, usually about 2 to 5 eV, plus higher kinetic energy peaks or lines characteristic of chemical species (e.g., chemical elements and/or their electron bondings) in the selected pixel area. In the case of rastering, the characteristic photoelectrons vary with any varying chemistry across the array of pixel areas, and the low energy electrons (commonly known as "secondary electrons") vary with topography, as well. Detection and/or analysis of the photoelectrons is used to provide information (e.g., spectral data) regarding the film at a selected pixel area or across the rastered array of areas of the film. There also may be Auger electrons which, for the present purpose, are included in the term "photoelectrons" as they are caused by the x-rays.

In one embodiment of the invention, an electron energy analyzer 54 receives a portion of the photoelectrons 52. The analyzer may be a known or desired type, generally either magnetic or electrostatic, which deflects the photoelectrons in a predetermined path 68 according to electron energy and then to a detector 70. A selected control, generally an electrical signal (current or voltage), is applied to the deflector to establish the amount of deflection and so is representative of selected energy of photoelectrons deflected in the predetermined path. In a magnetic analyzer such as a magnetic prism, a current signal through the magnet coils is appropriately selected, and in an electrostatic analyzer a deflecting voltage signal is selected.

One useful type of electrostatic energy analyzer is a cylindrical type described in U.S. Pat. No. 4,048,498, to Gerlach et al., issued 13 Sep. 1977 and entitled "Scanning Auger Microprobe with Variable Axial Aperture." In a preferable alternative, as shown in FIG. 6, the analyzer 54 is a hemispherical type as described in U.S. Pat. No. 3,766,381, to Watson, issued 16 Oct. 1973 and entitled "Apparatus and Method of Charge-Particle Spectroscopy for Chemical Analysis of a Sample." The analyzer also includes a lens system 56 such as an electrostatic lens for the input to the analyzer. The lens system 56 has a central axis 57 therethrough along which system 56 lies. The lens system 56 may combine objective and retarding functions to collect photoelectrons emitted from the effective pixel area and direct them into the analyzer in the desired kinetic energy range.

The electrostatic lens system 56 may be any conventional lens, for example, a PHI Omnifocus IV™ lens available from Physical Electronics Inc. The lens should include pairs of orthogonal deflection plates with applied voltages from a source 62. The voltages are selected, varied, or oscillated via the processor 76 in cooperative synchronization with positioning or rastering of the primary electron beam 20, under control of the processor, to centralize off-axis photoelectrons so that a substantial portion of the electrons reach the slit 84 and enter into the analyzer 54.

An alternative for the objective lens function is a magnetic lens, advantageously of a type variously known as an immersion lens, a single pole piece lens or a snorkel lens as described in U.S. Pat. No. 4,810,880, to Gerlach, issued 7 Mar. 1989 and entitled "Direct Imaging Monochromatic Electron Microscope."

Yet further, preferably, the lens system is an electrostatic lens with two spherical grids, similar to the Omega™ lens available from Physical Electronics Inc. Such a lens system is used in the PHI Quantum 2000 Scanning ESCA Microprobe™ available from Physical Electronics Inc.

Returning to FIG. 6, with a selected voltage from a voltage source 62 applied via lines 69 across the hemispheres 64, 66 of the analyzer, electrons of selected energy travel in a narrow range of trajectories 68 so as to exit the analyzer into the detector 70. The latter may be a conventional multichannel detector, for example, having 16 channels for detecting a small range of electron energies passed by the analyzer in slightly different trajectories. A further lens (not shown) may be placed between the analyzer and the detector, if desired or required for certain types of detectors.

Signals from the detector 70 corresponding to intensity of photoelectron input are carried on a line or lines 72 (via an appropriate amplifier, not shown) to an analyzing portion 74 of the processing unit 76 which combines control electronics and computer processing. The processing provides electron energy information and thereby information on components that are present and emitting the photoelectrons from the particular film surface area.

The information is stored, displayed on a monitor 78, and/or printed out in the form of images, numbers, and/or graphs. By cooperating the display (which herein includes the processing) with the electron beam directing means 28, 30, via line 80 from the processor to the controller 30, a mapping of the components in the selected or scanned surface area is effected and displayed. The mapping provides surface information corresponding to the selected pixel area location, or the rastered array of pixel areas on the film surface.

Other portions of the instrument 71, such as the secondary electron detector 88 and electron gun 98 providing ions 100, are used as described in U.S. Pat. No. 5,315,113.

According to the present invention, and advantageously used in the characterization of thin films, the lens system 56 is positioned at an analyzer angle for improved and faster data collection. The lens system 56 generally extends along a central axis 57 from a photoelectron receiving end 59 to an end coupled to hemispherical portions of the analyzer 54.

Preferably, according to the present invention as illustrated in FIG. 7A, the lens system 56 is positioned at an analyzer angle θ that is in the range of about 45 degrees to 90 degrees relative to the analysis plane of the instrument, corresponding to the sample surface being analyzed. The analyzer angle θ is represented by the angle between the plane of the sample surface 12 and the central axis 57 along which the lens system 56 lies. More preferably, the lens system 56 is positioned at an analyzer angle in the range of 60 degrees to 90 degrees; and even more preferably, the analyzer angle is about 75 degrees.

With the lens system 56 of the analyzer 54 positioned in such a manner, detection of a greater number of escaping photoelectrons from the film 2 upon irradiation by x-rays 36 is accomplished and a signal adequate for use in characterizing the film is attained in a considerably reduced amount of time relative to capture of such a signal when the lens system 56 is positioned at a low analyzer angle, e.g., less than 20 degrees, as generally represented in FIG. 7B. With use of such a high analyzer angle, component sensitivity in characterization of the film is improved. Further, detection limits for trace elements have also been shown to be better with use of a high analyzer angle relative to processes using a low analyzer angle.

Further, as shown in FIG. 7B, positioning of the lens system 56 at a low analyzer angle restricts the placement of the lens system relative to the sample. For example, a lens system is generally of a size such that at low analyzer angles, the lens system 56 must be positioned only near the edge of the film 2. As such, use of a low analyzer angle may restrict the size of film 2 that can be characterized. For example, positions of the film surface away from the lens system 56 shown in FIG. 7B at the end 61 of the film 2 are not easily characterized or effectively characterized with the lens system 56 positioned near the opposite edge of the film 2. With a high analyzer angle, any position on a large sample, such as semiconductor wafers and hard disk media, can be analyzed as the sample itself does not restrict where the lens system 56 can be placed.

With the lens system 56 positioned at a high analyzer angle (e.g., about 45 degrees to about 90 degrees), photoelectrons having corresponding photoelectron take-off angles relative to the film surface can be received by the lens system 56. For example, with the lens system positioned at 75 degrees, photoelectrons having a photoelectron take-off angle that falls in a cone of +/−20 degrees that is centered at 75 degrees can be detected using the analyzer. Likewise, if the analyzer is positioned at 60 degrees, photoelectrons escaping from the sample 2 at a photoelectron take-off angle that falls in a cone of +/−20 degrees that is centered at 60 degrees will be captured by the analyzer 54.

It will be recognized that use of the high analyzer angle $\theta$, e.g., in the range of about 45 degrees to about 90 degrees, relative to the analysis plane, results in an analysis depth(d) as shown in FIG. 7A that is much deeper than the analysis depth(d) shown in FIG. 7B when a low analyzer angle is utilized. As such, the signal generated based upon the detected photoelectrons results in data that includes contributions from the film 2 as well as the substrate 19 on which the film 2 is formed. Such depth is beneficial in the data reduction processes used for film characterization as will be apparent from the description herein.

With surface measurements collected as described herein, e.g., utilizing an analysis system 1 as shown in FIG. 1, the exemplary film characterization method 100 as shown in FIG. 2 may be performed to determine one or more characteristics of the film 2. The film characterization method 100 generally includes the provision of measured spectral peak shape(s) (block 102) for use in later comparison to acquired spectra, e.g., spectra acquired in real time during a manufacturing process.

The measured spectral peak shape(s), also referred to herein as basis spectra, (i.e., non-modeled and non-theoretical peak shapes) are preferably peak shapes determined experimentally (e.g., the process as described with reference to FIGS. 8B–8D) and are representative of at least one component of a particular type of film, where the film was formed by a particular process defined by a predefined set of processing conditions. For example, the particular process may be a process used in a manufacturing line for the formation of a thin gate oxide film formed on a silicon substrate in the manufacture of integrated circuits. Such measured spectral peak shapes, i.e., measured basis spectra, may be, for example, peak shapes associated with silicon in the gate oxide film and the silicon in the substrate upon which the film is formed when the film is silicon oxynitride film formed on a silicon substrate. Generally, the relative area under each of the peak shapes gives the relative abundance of the component in the analysis volume, e.g., in the film and at least a portion of the underlying substrate to a particular depth.

The film characterization method 100 further includes the acquisition of surface spectral measurements for an additional film formed on an underlying substrate (block 106); the additional film being formed using the particular process defined by the same set of predefined processing conditions used in forming the film from which the measured spectral peak shapes are determined (block 102). In other words, the measured spectral peak shapes are provided based on a film that is manufactured under the same, or at least substantially similar, process conditions as the film to be characterized and for which surface measurements are provided as shown in block 106. The acquired spectrum includes at least one peak area representative of the at least one component for which measured spectral peak shapes are provided per block 102, At least the measured spectral peak shape(s) provided per block 102 are compared to the acquired spectrum (block 106), or at least a portion thereof (block 108). For example, in one embodiment, the measured spectral peak shape(s) (provided per block 102) and a spectral background are compared to the acquired spectrum (block 106), or at least a portion thereof, as shown by block 108. For example, the measured peak shape(s) and the spectral background may be simultaneously fitted to the surface measurement data acquired for a film to be characterized. Such a comparison may be accomplished using a non-linear least squares fitting algorithm or any other comparison process that would provide a desired comparison result, e.g., a neural network, a linear least squares algorithm, sector analysis, etc.

In other words, any suitable fitting algorithm may be used to judge which combination of basis spectra (i.e., the measured spectra provided per block 102 represented by the measured spectral peak shapes) provides the best fit. Least squares is a generally accepted criteria to determine "goodness" of fit, however, any criterion that provides for such a determination can be used, e.g., the sum of absolute values of the difference between certain modeled, measured and/or acquired spectra.

In this embodiment, both the measured peak shapes and a spectral background shape are fitted to the acquired spectral data. Generally, the spectral background is that portion of the spectrum acquired according to the present invention that is underlying the spectral peak(s) of interest, and which is not related to the concentration of the sample-component of interest. For example, the spectral background is generally representative of, at least in part, inelastically scattered electrons (e.g., electrons that have lost energy). In one embodiment, a spectral background shape for use in the film characterization method 100 is calculated from the acquired spectrum (block 106) provided for the film to be characterized (e.g., an integration of the acquired spectrum as described below).

In another embodiment, the spectral background may be provided or calculated from a spectrum provided for a film processed under the same conditions as the film for which the measured spectral peak shapes are provided.

In an alternate embodiment, the spectral background may be subtracted from the acquired data (e.g., that acquired per block 106). Thereafter, the measured spectral shapes may be fitted to the acquired spectral data from which the background was subtracted. In other words, the spectral background may be subtracted from the acquired spectral data prior to the fitting algorithm being used.

One or more characteristics of the film to be characterized are then determined based on the comparison (block 110). For example, the comparison may be used and/or operated upon by one or more algorithms or routines for determination of film thickness.

Optionally, the characteristic determined based on the comparison (block 110) may be used for one or more other purposes, such as determining other characteristics of the film (block 112). For example, in various embodiments described herein, film thickness is used with one or more other spectra to provide dose concentrations of a component of the film, is used to determine thickness uniformity, is used to perform and determine dose concentration uniformity across a wafer upon which the film to be characterized is deposited, etc.

Further, the characteristics determined based on the comparison (block 110) may be used in conjunction with one or more other processes or algorithms, or alone, to detect a process excursion. For example, a thickness measurement may indicate that the manufacturing tool or process used to form the film which is being characterized has deviated from allowable predetermined thicknesses so as to indicate that the process is not operating effectively. As such, the manufacturing process may be appropriately controlled, adjustments to parameters may be made, indications that the manufacturing line should be halted, or any other resultant measure necessary to effectively proceed in the manufacturing process may be performed.

The film characterization method 100 will become clearer upon further description with regard to the thin dielectric film characterization method 200 as generally shown in FIG. 8A and which is described in further detail with reference to FIGS. 8-10. The thin dielectric film characterization method 200 of FIG. 8A is performed to determine thickness of a silicon oxynitride film formed on a silicon substrate by a particular process defined by a set of processing conditions. For example, a manufacturing line may form a silicon oxynitride layer on wafers which require inline monitoring of the process so as to detect whether any excursions from the desired process are occurring. The present invention, including the thin dielectric film characterization method 200, may be used to determine silicon oxynitride film characteristics for use in detecting such a process excursion.

One skilled in the art will recognize that, although the method 200 is described with particular reference to a silicon oxynitride film, the characterization processes described herein can be extended to other films as well. In no manner is the present invention limited to the analysis of silicon oxynitride films. For example, as previously mentioned, various other thin dielectric films (e.g., silicon oxide, tantalum nitride, tantalum oxide, etc.) may be characterized using the concepts described herein.

As shown generally in the flow diagram of FIG. 8A, spectral data is provided for use in the thin dielectric film characterization method 200. Such spectral data is illustratively shown in the spectra diagram 280 of FIG. 10.

According to the method 200 shown in FIG. 8A, with use of the Si2p region of the XPS surface measurement spectrum for a silicon oxynitride film to be characterized, a calculation of the thickness (block 210) of the silicon oxynitride film can be performed with high precision. Film thickness of the silicon oxynitride film can be calculated according to the following equation:

$$\text{Film Thickness} = \lambda \sin(\theta) \ln[(K*(\text{SiON})/(\text{Si})) + 1 - L\text{Corr}]$$

The above film thickness equation is a standard equation used to determine the thickness of a thin layer using XPS surface measurements, with an additional term, LCorr, that compensates for spectral contributions of multiple x-ray lines from nonmonochromated x-ray sources, e.g., magnesium x-ray sources. The values for $\lambda$ and K impact the accuracy but not the precision of the thickness measurement. A value for $\lambda$ can be obtained from IMFP (inelastic mean free path) model calculations using NIST database #71. Such a value for $\lambda$ may be, for example, 34 angstroms.

The constant K can be determined by analyzing a silicon oxynitride film of known thickness as determined by, for example, TEM measurements. Such a TEM measurement would be made once for each specific particular process. While the TEM measurement may limit the accuracy of the method, it does not limit precision of measurement, which is desirable. In other words, although accuracy is important, precision in obtaining the same measurement for a particular film over and over again is generally more desirable than whether the actual measurement is correct or not correct, as long as the accuracy is within acceptable limits.

The constant Lcorr can be determined by comparing film thickness is results from monochromated and nonmonochromated x-ray sources on the same samples and adjusting the constant to achieve the same thickness result.

As is clear, the peak area ratio of SiON/Si is the only other non-constant in the film thickness equation. Therefore, the measurement or ratio of these two peak areas (i.e., the ratio of the silicon peak area for the SiON film to the silicon peak area for the silicon substrate underlying the SiON film) defines the precision of the thickness measurement.

The key to achieving measurement precision beyond that expected with standard XPS practice and to produce precise results lies in, for example, the choice of instrument parameters used for collecting the data and in also the method of measuring the peak areas which form the ratio of SiON/Si. Preferably, although not necessarily, the XPS spectra are collected with the instrument conditions optimized for elemental sensitivity at the expense of energy resolution and surface sensitivity. This, as described previously, deviates from standard practice.

For example, preferably, as previously described herein, a high analyzer angle $\theta$ that is in the range of about 45° to about 90° relative to the sample surface plane is used for collection of surface spectral measurements. More preferably, the analyzer angle is in the range of about 60° to about 90°; and even more preferably, the analyzer angle is about 75°. Such an analyzer angle is chosen to maximize signal, maximize analysis depth, allow large samples, minimize interference from photoelectron diffraction, and minimize sensitivity to angle variations.

With the analyzer of the XPS system positioned in such a manner, detection of a greater number of escaping photoelectrons from the film and the underlying substrate upon irradiation by x-rays is accomplished. A signal adequate for use can be acquired in a considerably reduced amount of time relative to capture of such a signal when the lens of the system is positioned at a low analyzer angle, e.g., less than 45°.

Yet further, the selection of the x-ray source may also be important in collection of spectral data. Preferably, a low energy x-ray source defined herein as an energy source operating at low energies of less than 2,000 eV is utilized according to the present invention. Such lower energy x-ray sources are used in XPS systems because they provide less chance of sample damage, higher sensitivity, and better energy resolution and accuracy. For these reasons, the K-alpha emission lines of aluminum and magnesium are most often used. Further, non-monochromatic (as opposed to monochromatic) sources may be used advantageously from a cost and measurement speed perspective.

Figure 10:
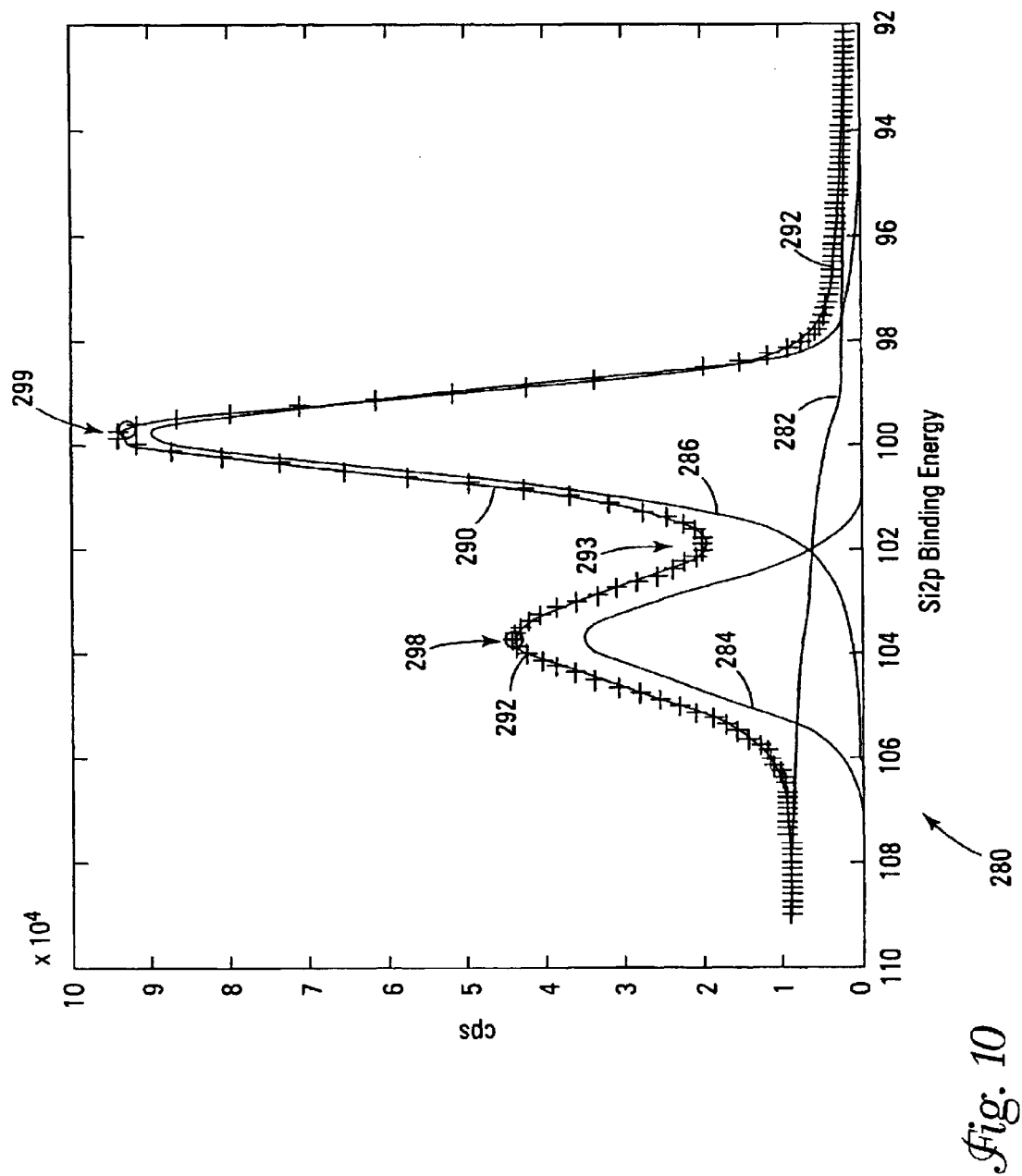
FIG. 10 is a diagram for use in illustrating the methods described in FIGS. 8A and 9.

The problem with effectively measuring the peak area ratio of SiON/Si from the acquired surface measurement spectra is illustrated in FIG. 10 along with a process for effectively providing such a ratio for precise measurements. The problem in measuring the peak area ratio of SiON/Si lies, at least partially, in the fact that the acquired surface measurement spectrum 292 includes two silicon peak areas 298 and 299. Silicon peak area 298 is representative of the silicon content of the silicon oxynitride film. Silicon peak area 299 is representative of the silicon content of at least a portion of the underlying silicon wafer. One will recognize that the ratio cannot be attained effectively due to the overlap 293 between the peak areas 298 and 299.

Existing data reduction methods employ software tools for spectral background subtraction and peak fitting for separating the silicon peak areas to obtain the SiON/Si ratio. Such existing data reduction methods require frequent operator input making the results operator-dependent and less precise. For example, such existing data reduction methods employ theoretical spectral peak shapes allegedly representative of the silicon content in a silicon oxynitride film and representative of silicon in an underlying silicon wafer. However, as described above, such theoretical peak shapes must be selected and operator input is used to fit such theoretical peak shapes to the acquired surface measurement spectrum 292 after subtraction of a spectral background component therefrom. Existing methods also have a large number of degrees of freedom which degrade precision.

The present invention does not utilize theoretical peak shapes nor does it utilize operator input to provide background subtraction or peak fitting of such theoretical peak shapes. Rather, the present invention, at least in one embodiment thereof, eliminates operator input and uses a comparison algorithm that enhances the data quality, yielding a film thickness measurement with desirable precision. This embodiment of the present invention for determination of film thickness is shown and shall be further described with reference to the thin dielectric film characterization method 200.

In the thin dielectric film characterization method 200, measured spectral peak shapes (i.e., measured basis spectra) representative of the silicon content of a silicon oxynitride film 284 and of the silicon content of a silicon substrate underlying the silicon oxynitride film 286 are provided (block 202). The experimentally determined peak shapes (i.e., measured basis spectra) are important to the present invention as they include contributions of the analyzer as well as the sample. Therefore, it is important that the peak shapes are measured on the same type of instrument and under the same conditions as any subsequent analyses that uses such measured peak shapes for analysis.

As used herein, when a process is performed to form a film under the same particular process conditions as another film was formed (e.g., to form a film to be characterized under the process conditions as used to provide a film that is used for providing the measured basis spectra), it is to be understood that the process conditions and tools used to carry them out may be either the same tool or a tool of substantially the same type. One skilled in the art will recognize that the conditions may be substantially the same without rendering the processes described herein ineffective.

In one example, a measured spectral peak shape 286 representative of the silicon content of the silicon substrate may be provided based on surface is spectral measurements of a silicon wafer being used in the particular process for forming the film to be characterized. In such a manner, an actual representation of the silicon content, as opposed to a theoretical representation, is obtained.

Likewise, a measured silicon spectrum 284 representative of the silicon 20 content in the silicon oxynitride film formed according to the particular process under the predefined set of process conditions may be acquired. For example, such a silicon spectrum 284 representative of the silicon content for the silicon oxynitride film may be measured by forming the silicon oxynitride on a silicon substrate under the set of predefined conditions. Thereafter, surface measurements are taken therefrom to obtain a silicon spectrum representative of the silicon content of the silicon oxynitride film in addition to the underlying silicon substrate. The silicon spectrum representative of the silicon content for the silicon oxynitride film can then be attained by subtracting the silicon spectrum for the silicon substrate from the silicon spectrum representative of the silicon content of the silicon oxynitride film and the underlying silicon substrate.

In addition, there are other ways to obtain the basis spectra, i.e., the measured spectral silicon peak shapes. For example, the substrate silicon spectrum could be obtained from a chemically etched silicon wafer, the etch having removed all oxide.

Further, the oxide silicon spectrum, i.e., the spectrum representative of the silicon in the silicon oxynitride film, could be obtained from a thick oxide.

Figure 8B:
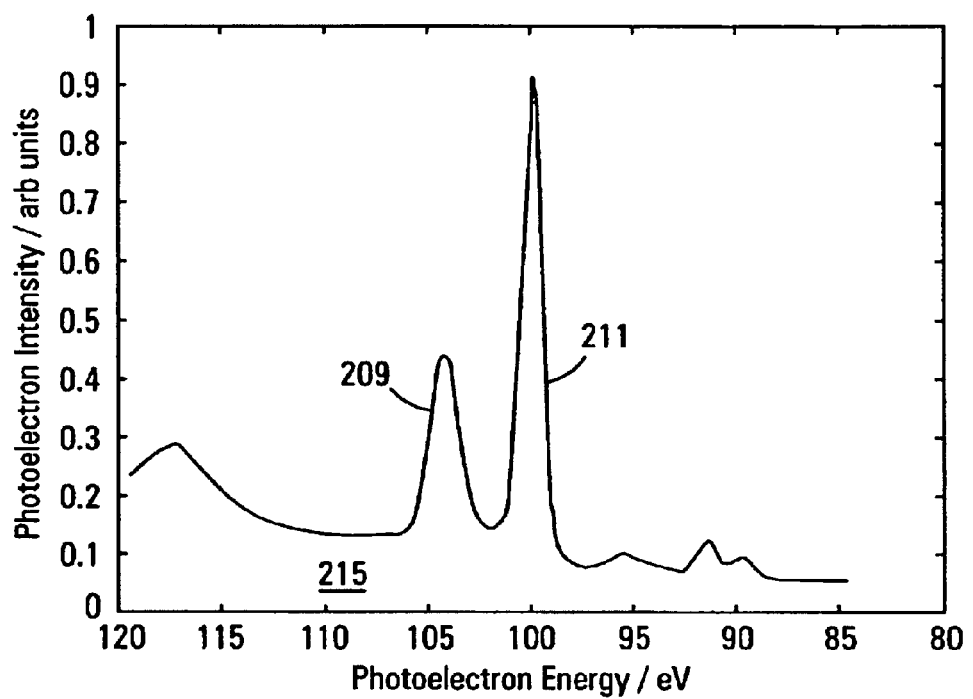
FIGS. 8B–8D are illustrative spectral diagrams for use in illustrating one exemplary embodiment for providing basis spectra according to the present invention as generally shown in FIG. 8A.

Yet further, preferably, the basis spectra can be obtained as shall be described with reference to FIGS. 8B–8C. For example, a high resolution Si2p spectrum may be provided as shown in FIG. 8B. As used in the context of this process, a high resolution spectrum is a spectrum obtained at a resolution that is greater than the resolution of the acquired spectrum acquired for the film to be characterized. Preferably, the resolution is such that the narrow spectral peak 209 representative of the silicon in the silicon oxynitride film and the narrow spectral peak 211 representative of the silicon in the substrate thereunder are easily separated (i.e., the peaks have very little overlap after the spectral background 215 is subtracted).

Figure 8C:
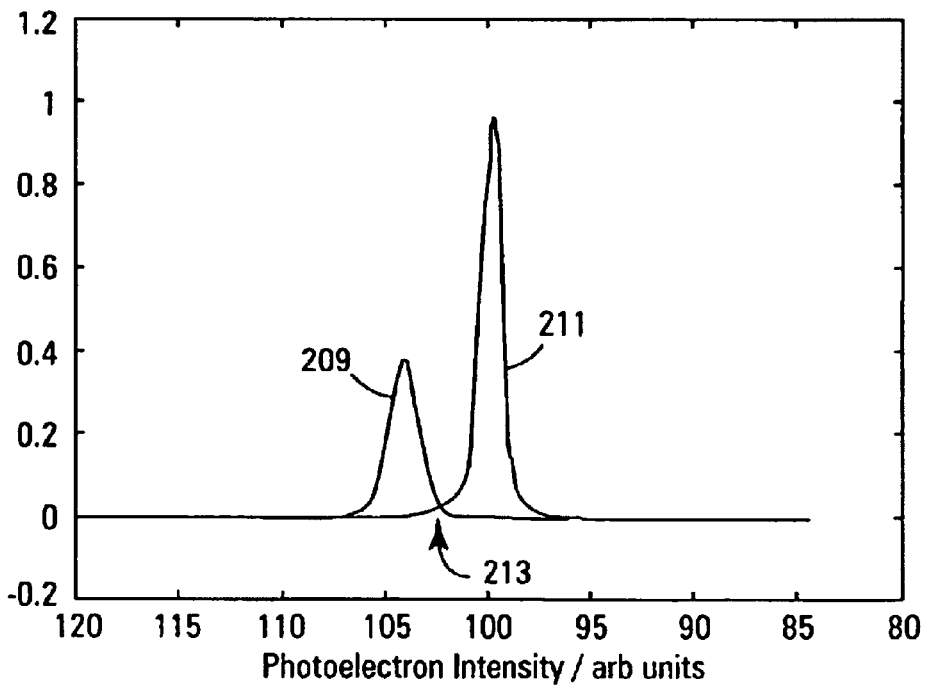
Figure 8D:
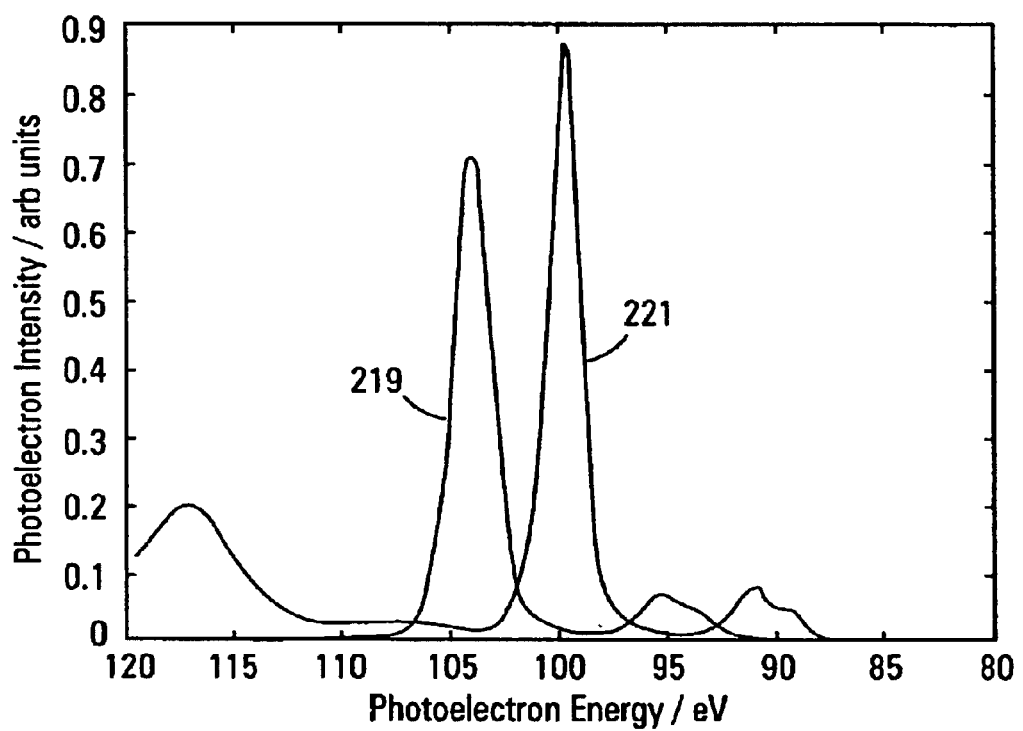

FIG. 8C shows the spectral peaks 209 and 211 separated. Note that with the spectral background 215 subtracted, that very little overlap 213 between the spectral peaks 209 and 211 exists. As such, they are easily separated.

Following separation of the narrow spectral peaks 209 and 211, an instrumental broadening function is applied to the narrow spectral peaks 209 and 211 to match the resolution of the acquired spectrum acquired for the film to be characterized. Such broadening functions are known to those skilled in the art and will not be described in detail herein. For example, such functions have been described in Hufner and Wertheim, Phys. Rev. B11, 678 (1975). The resultant measured basis spectra 219 and 221 can then be used in the characterization method 200.

Generally, experimentally determined (i.e., measured) basis spectra are used rather than the conventionally available universal peak shapes. Universal shapes can never account for the peculiarities of the energy analyzer which influence peak shape in subtle ways. The same measured basis spectra may be used for the same type of machines, or in the alternative such basis spectra may be experimentally determined for each individual machine even if such machines are of the same type.

With the measured spectral peak shapes 284 and 286 provided (e.g., provided as described above or as provided in any other known measured or experimental manner related to the particular process used in forming the silicon oxynitride film), surface measurements are acquired for a film to be characterized and an acquired spectrum associated therewith is provided (block 206). In other words, real surface measurement data for the Si2p region of the XPS spectrum is acquired. Such an acquired spectrum 292 includes overlapping silicon peak areas 298 and 299 (block 206).

The acquired spectrum 292 for the silicon oxynitride film to be characterized (e.g., thickness to be determined) is compared to the measured silicon peak shapes and, and preferably a spectral background (e.g., preferably, simultaneously) to extract and/or separate acquired silicon peak areas for each of the silicon oxynitride film and the underlying silicon substrate (block 208). The silicon peak areas can then be used to provide the SiON/Si ratio for determination of thickness as described herein. One embodiment of such a comparison process will be described in further detail below with reference to the spectra comparison process 208 shown in FIG. 9.

Using the extracted acquired silicon peak areas (i.e., a silicon peak area for the silicon oxynitride film and another silicon peak area for the underlying silicon substrate), a precise ratio for use in the film thickness equation is provided. As such, film thickness based on the comparison performed as shown in block 208 can be determined per block 210.

Thereafter, film thickness may optionally be utilized for one or more other purposes (block 212). For example, as previously described herein, film thickness may be used to detect a process excursion.

Further, by repeating the thickness measurement process for various locations of the film a thickness uniformity for the wafer may be determined. For example, sample (e.g., film) motion can be used to cover a much larger area, e.g., obtain measurements from a larger area. In other words, thickness of the film can be determined for the larger area across the thin film. With the thickness known, the degree of uniformity in the thickness across the film can be determined.

Yet further, the thickness measurement may be used to determine other characteristics of the film such as concentration of nitrogen in the film as shall be described with reference to FIGS. 14 and 15.

Preferably, a spectral background (e.g., such as that previously described herein) is used in the comparison process and is calculated from the acquired spectrum. For example, an integration of the acquired spectrum and operation thereon in accordance with the teachings of D. A. Shirley as described in D. A. Shirley, Phys. Rev. B5 4709 (1972) provide a spectral background shape that can be used in the comparison process.

Figure 9:
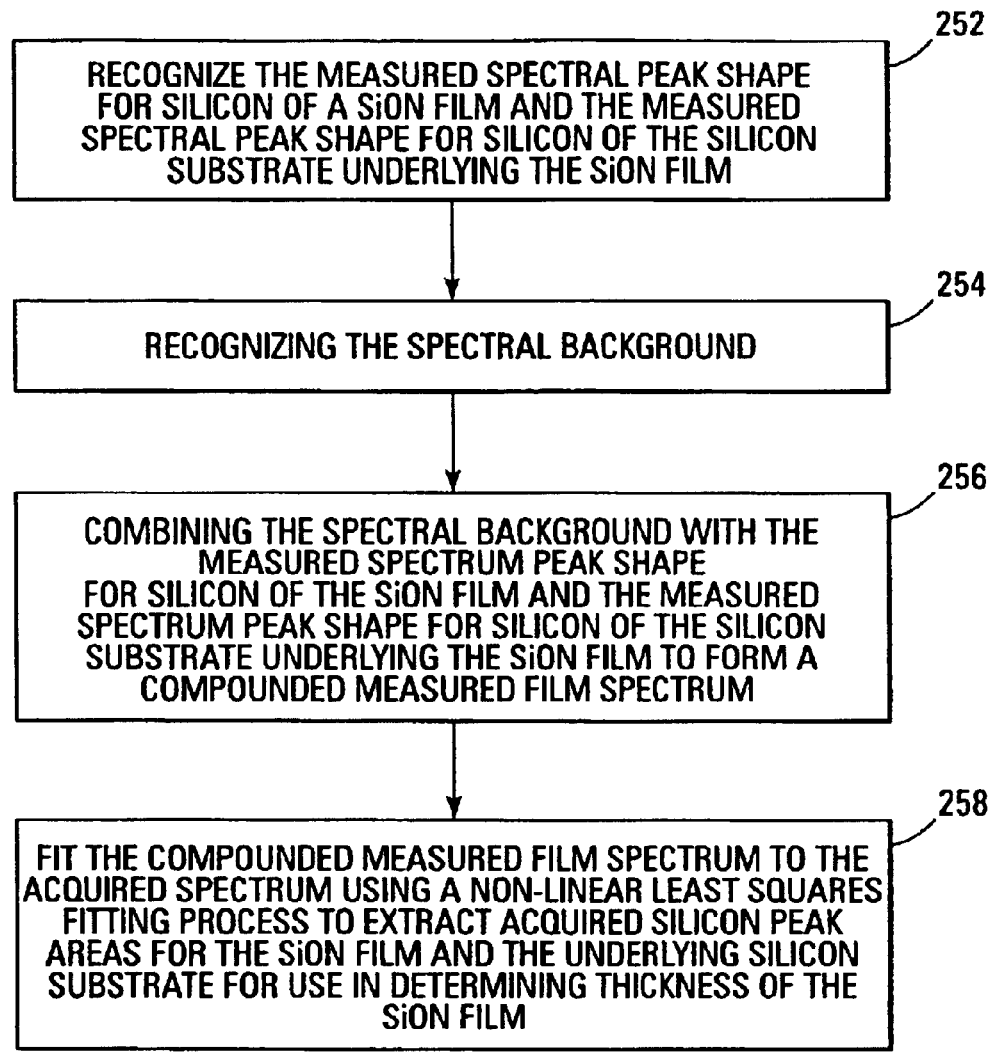
FIG. 9 is one exemplary embodiment of a spectral comparison process shown generally in FIG. 8A.

FIG. 9 shows one illustrative spectra comparison process 208 where the measured spectral peak shapes 284, 286 and a spectral background calculated from the acquired spectrum are compared with the acquired spectrum 292 of the film to be characterized. The process 208 is started by the recognition of the measured spectral peak shape 286 representative of the content of silicon in the silicon oxynitride film and the measured spectral peak shape 284 representative of the silicon content of the silicon substrate underlying the silicon oxynitride film (block 252). Further, the process 208 recognizes the spectral background 282 (block 254).

With such measured spectral peak shapes 284, 286 and spectral background 282 recognized, the spectral background 282 and the measured spectra peak shapes 284, 286 are combined resulting in a compounded measured film spectra 290 as shown in FIG. 10 (block 256). The compounded measured film spectra 290 can then be compared to the acquired spectrum 292 (e.g., fitted) (block 258). For example, the compounded measured film spectra 290 may be fitted using a non-linear least squares fitting process. Such least squares fitting processes are know in the art and therefore will not be described in detail herein. It should be recognized that the spectral background 282 is fitted simultaneously with the measured spectral peak shapes 284, 286 to the acquired spectrum 292 for the film to be characterized. Preferably, the spectral background is recalculated during the fitting process. Preferably, such spectral background recalculation is performed during each iteration of the fitting process.

With the measured spectral peak shapes 284, 286 known, and with such compounded measured film spectra 290 fitted to the acquired spectrum 292 of the film to be characterized, an acquired silicon peak area representative of the silicon content in the silicon oxynitride film and a peak area representative of the silicon content in the underlying silicon wafer can be separately provided. Such peak areas can then be used in the ratio for calculating film thickness as described herein (e.g., per the equation presented above).

Figure 3:
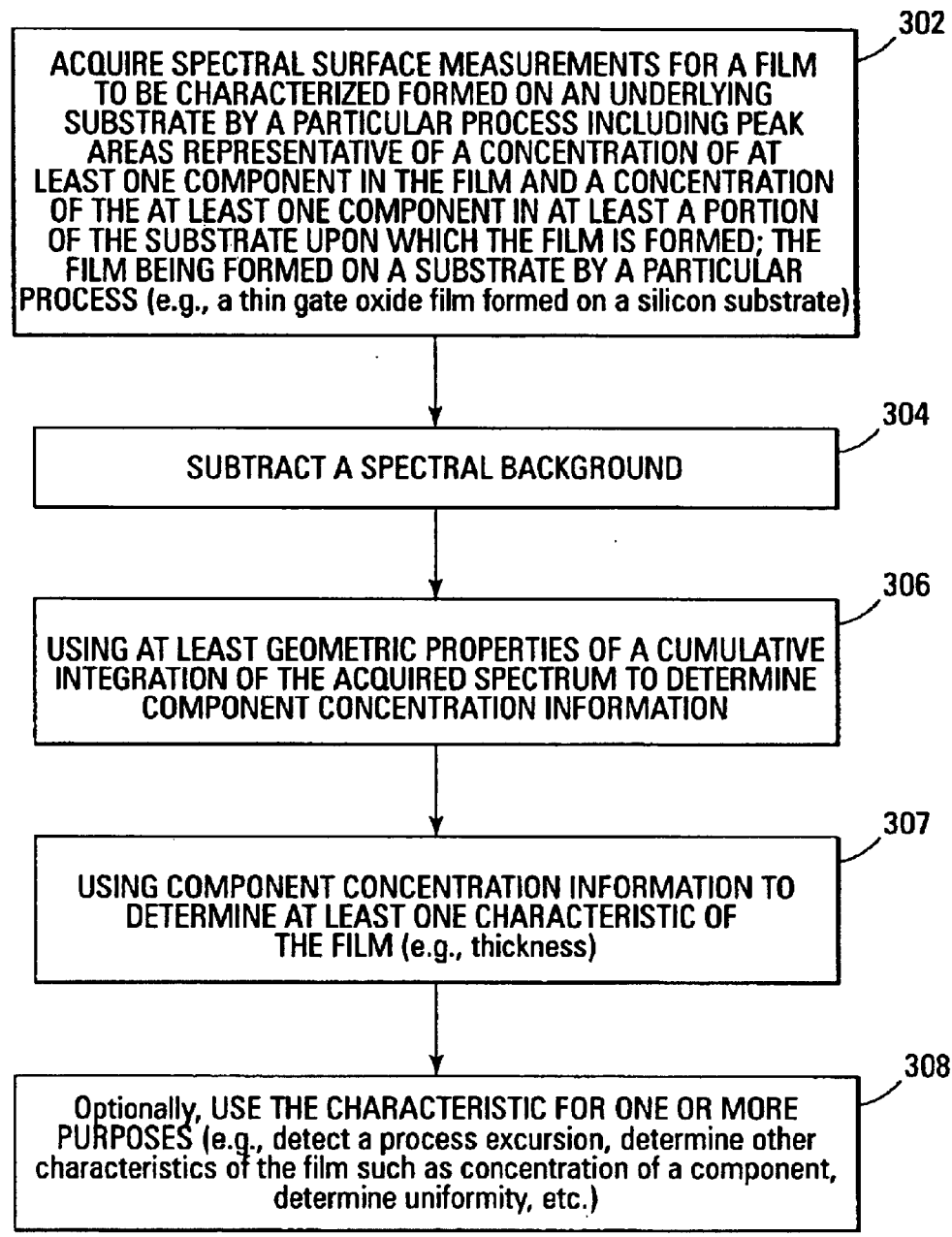
FIG. 3 is an exemplary diagram of an alternate film characterization method that may be carried out by the illustrative analysis system shown in FIG. 1.

Further, with surface measurements collected as described herein, e.g., utilizing an analysis system 1 as shown in FIG. 1, another exemplary film characterization method 300 as shown in FIG. 3 may be performed to determine one or more characteristics of the film 2. The method 300 can determine thickness from the same acquired spectrum used in the method 100, e.g., the spectrum including overlapping acquired peaks such as those peaks representative of the silicon in a silicon oxynitride film and the silicon of the substrate on which the film is formed. However, the characterization method 300 does not require the measurement and extraction of pure component basis spectra (e.g., the measured spectral peak shapes) which were previously described herein for use to fit the acquired Si2p region of the XPS spectrum.

In other words, the extraction of peaks representative of the silicon in a silicon oxynitride film and the silicon of the substrate on which the film is formed is based solely on the acquired spectrum (e.g., a cumulative integration of the acquired spectrum). As used in the context of this process, extraction solely from the acquired spectrum refers to the extraction of component concentration information (e.g., ratio of silicon in a silicon oxynitride film to silicon in the substrate on which the film is formed) without use of basis spectra such as the conventionally used model or synthetic basis spectra (e.g., spectra not determined based on any specific tool and/or process conditions) and without the use of measured basis spectra such as determined or generated as described herein (e.g., experimentally determined such as with use of the high resolution spectrum and broadening function as described with reference to FIGS. 8B–8D).

Further, since no fitting of the spectral components is required (not even to theoretical or "synthetic" model spectra), the calculation time for the characterization method 300 is considerably reduced. For example, the calculation time may be reduced by as much as 100 times over the fitting process used in method 100. Yet further, thickness determination is much less sensitive to the amount of nitrogen in a silicon oxynitride film when such a film type is being characterized.

The method 300, like method 100, is applicable to the characterization of many different types of films and any listing herein is not to be taken as being limiting on the present invention. For example, method 300 is generalizable to any thin film (e.g., including a stack of layers) where the surface and underlying substrate (e.g., one or more films, structures or other regions) can be measured using XPS or other spectroscopy techniques such as AES. In other words, the thickness determination methods described herein are applicable to other films in a manner substantially similar to that described herein with respect to the determination of thickness for silicon oxide or silicon oxynitride films on silicon. Further, the data analysis techniques described herein may be used with spectral data acquired from any number of different spectroscopy methods and not only XPS techniques described herein.

The film characterization method 300 generally includes the acquisition of spectral surface measurements to provide an acquired spectrum for a film to be characterized (block 302). The film to be characterized is formed on a substrate using a particular process defined by a set of predefined processing conditions. Generally, the acquired spectrum includes at least one spectral peak representative of a concentration of at least one component in the film to be characterized and at least an additional spectral peak representative of the at least one component in at least a portion of the substrate upon which the film is formed.

For example, the particular process may be a process used in a manufacturing line for the formation of a thin gate oxide film formed on a silicon substrate in the manufacture of integrated circuits. The acquired spectrum may include an Si2p spectrum region that includes spectral peak shapes associated is with silicon in the gate oxide film and the silicon in the substrate upon which the film is formed. Generally, the relative area under the peak shapes gives the relative abundance of the silicon component in the analysis volume, e.g., in the film and at least a portion of the underlying substrate to a particular depth.

The characterization method 300 further includes the subtraction of a spectral background (block 304) from the acquired spectrum. Generally, as previously described herein the spectral background is that portion of the spectrum acquired according to the present invention that is underlying the spectral peak(s) of interest, and which is not related to the concentration of the sample component of interest, e.g., silicon. Preferably, the spectral background is a Shirley calculated spectral background.

After subtraction of the spectral background, the film characterization method 300 uses at least geometric properties of a cumulative integration of the acquired spectrum to extract component concentration information from the acquired spectrum (block 306). For example, the component concentration information may be a ratio of a concentration of at least one component in the film to be characterized to a concentration of the at least one component in at least a portion of the substrate upon which the film is formed. Thereafter, such component concentration information may be used to determine one or more characteristics of the film to be characterized (block 307). For example, the component concentration information may be used and/or operated upon by one or more algorithms or routines for determination of film thickness.

Optionally, the characteristic determined based on the component concentration information (block 307) may be used for one or more other purposes (block 308), such as determining other characteristics of the film. For example, in various embodiments described herein, film thickness is used with one or more other spectra to provide dose concentrations of a component of the film, is used to determine thickness uniformity, is used to perform and determine dose concentration uniformity across a wafer upon which the film to be characterized is deposited, etc.

Further, the characteristics determined based on the component concentration information (block 307) may be used in conjunction with one or more other processes or algorithms, or alone, to detect a process excursion. For example, a thickness measurement may indicate that the manufacturing tool or process used to form the film which is being characterized has deviated from allowable predetermined thicknesses so as to indicate that the process is not operating effectively. As such, the manufacturing process may be appropriately controlled, adjustments to parameters may be made, indications that the manufacturing line should be halted, or any other resultant measure necessary to effectively proceed in the manufacturing process may be performed.

Figure 11:
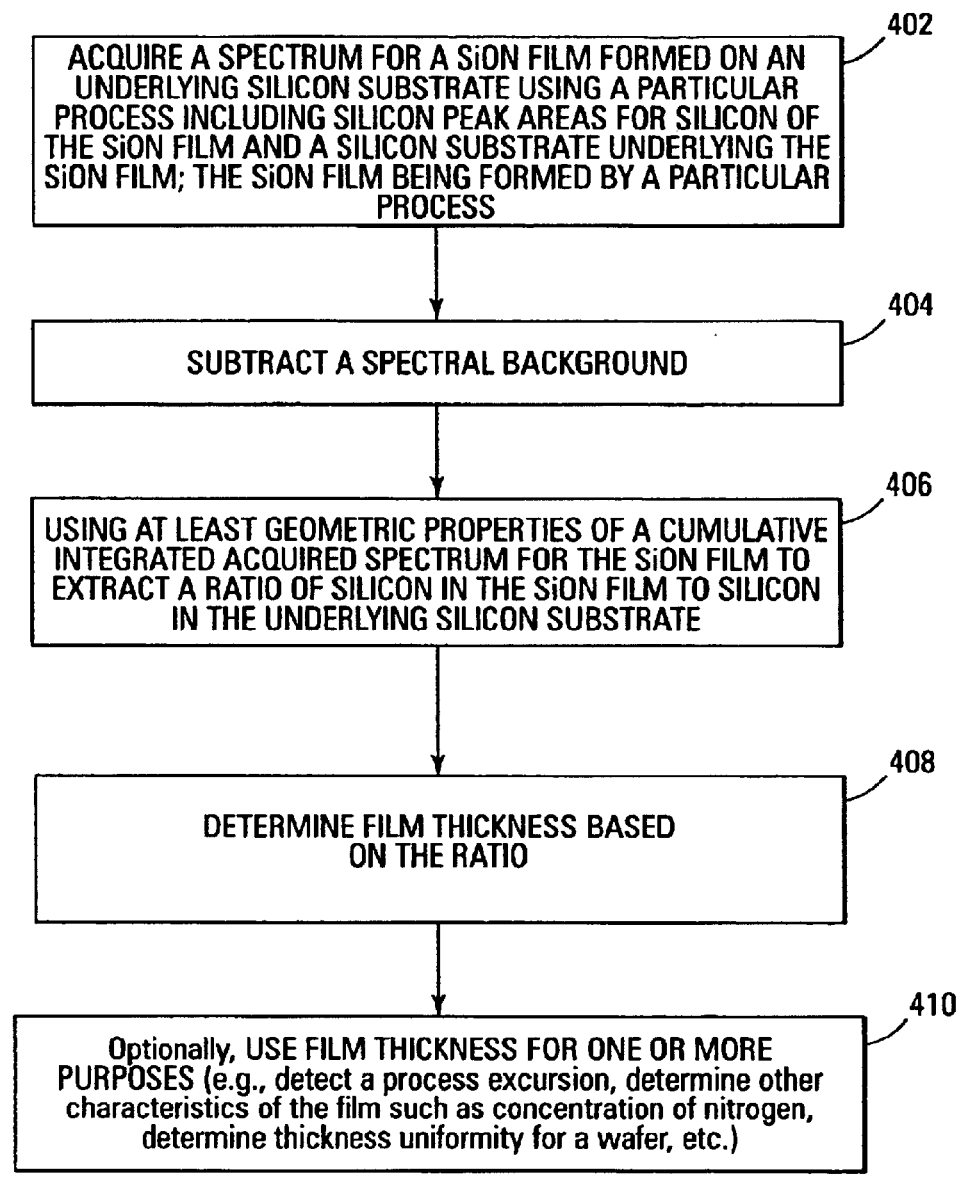
FIG. 11 is an illustrative flow diagram of another alternate embodiment of a thin dielectric film characterization method for use in determining thickness of a film according to the present invention.

The film characterization method 300 will become clearer upon further description with regard to the thin dielectric film characterization method 400 as generally shown in FIG. 11 and which is described in further detail with reference to FIGS. 11–13. The thin dielectric film characterization method 400 of FIG. 11 is performed to determine thickness of a silicon oxynitride film formed on a silicon substrate by a particular process defined by a set of processing conditions. For example, a manufacturing line may form a silicon oxynitride layer on wafers which require inline monitoring of the process so as to detect whether any excursions from the desired process are occurring. The present invention, including the thin dielectric film characterization method 400, may be used to determine silicon oxynitride film characteristics for use in detecting such a process excursion.

One skilled in the art will recognize that although the method 400 is described with particular reference to a silicon oxynitride film, that the characterization processes described herein can be extended to other films as well. In no manner is the present invention limited to the analysis of silicon oxynitride films. For example, as previously mentioned, various other thin dielectric films (e.g., silicon oxide, tantalum nitride, tantalum oxide, etc.) may be characterized using the concepts described herein.

As shown generally in the flow diagram of FIG. 11, spectral data is provided (block 402) for use in the thin dielectric film characterization method 400. Such spectral data is illustratively shown in the insert spectral diagram 470 of FIG. 13.

According to the method 400 shown in FIG. 11, with use of the Si2p spectrum region 471 of the XPS surface measurement spectrum for a silicon oxynitride film to be characterized (block 402), a calculation of the thickness (block 408) of the silicon oxynitride film can be performed with high precision. Film thickness of the silicon oxynitride film can be calculated according to the following equation:

$$\text{Film Thickness} = \lambda \sin(\theta) \ln[(K^*(\text{SiON})/(\text{Si})) + 1 - L\text{Corr}]$$

The above film thickness equation is a standard equation used to determine the thickness of a thin layer using XPS surface measurements, with an additional term, LCorr, that compensates for spectral contributions of multiple x-ray lines from nonmonochromated x-ray sources, e.g., magnesium x-ray sources. As discussed herein, the peak area ratio SiON/Si (i.e., the ratio of the silicon peak area for the SiON film to the silicon peak area for the silicon substrate underlying the SiON film) defines the precision of the thickness measurement.

Preferably, although not necessarily, the XPS spectra are collected with the instrument conditions optimized for elemental sensitivity at the expense of energy resolution and surface sensitivity in a manner as described herein with reference to methods 100 and 200. For example, preferably, as described herein, a high analyzer angle θ that is in the range of about 45° to about 90° relative to the sample surface plane is used for collection of surface spectral measurements.

As previously described herein, the problem with effectively measuring the peak area ratio of SiON/Si from the acquired spectrum 471 lies, at least partially, in the fact that the acquired surface measurement spectrum 471 includes two silicon peak areas 472 and 474 (i.e., representative of the silicon content of the silicon oxynitride film and representative of the silicon content of at least a portion of the underlying silicon wafer) with an overlap therebetween.

The present invention, at least in this embodiment, uses an algorithm that operates on the acquired spectrum 471 alone (with no fitting to other spectral components) to enhance the data quality, yielding a film thickness measurement with desirable precision. This embodiment of the present invention for determination of film thickness is further described with reference to the thin dielectric film characterization method 400.

In the thin dielectric film characterization method 400, the calculated spectral background is subtracted (block 404) from the acquired spectrum 471. Generally, as previously described herein the spectral background subtracted is a function of an integrated acquired spectrum and represents that portion of the spectrum acquired according to the present invention that is underlying the spectral peak(s) of interest, and which is not related to the concentration of the sample component of interest, e.g., silicon.

After subtraction of the spectral background, the film characterization method 400 applies an algorithm (e.g., a tangent intersection algorithm as shown and described with reference to FIGS. 12 and 13) which uses at least geometric properties of a cumulatively integrated acquired spectrum that provides cumulative spectral intensities at the peaks and valleys of the acquired spectrum. The algorithm extracts a ratio of the concentration of silicon in the film to be characterized to a concentration of the silicon in at least a portion of the substrate upon which the film is formed. In other words, a ratio of the spectral intensities of the spectral peak areas 472, 474 is extracted for use in the above mentioned thickness algorithm. As such, a film thickness based on the ratio can be determined as shown in block 408.

Thereafter, film thickness may optionally be utilized for one or more other purposes (block 410) as described herein. For example, as described herein, film thickness may be used to detect a process excursion. Yet further, is the thickness measurement may be used to determine other characteristics of the film such as concentration of nitrogen in the film as shall be described with reference to FIGS. 14 and 15.

Figure 12:
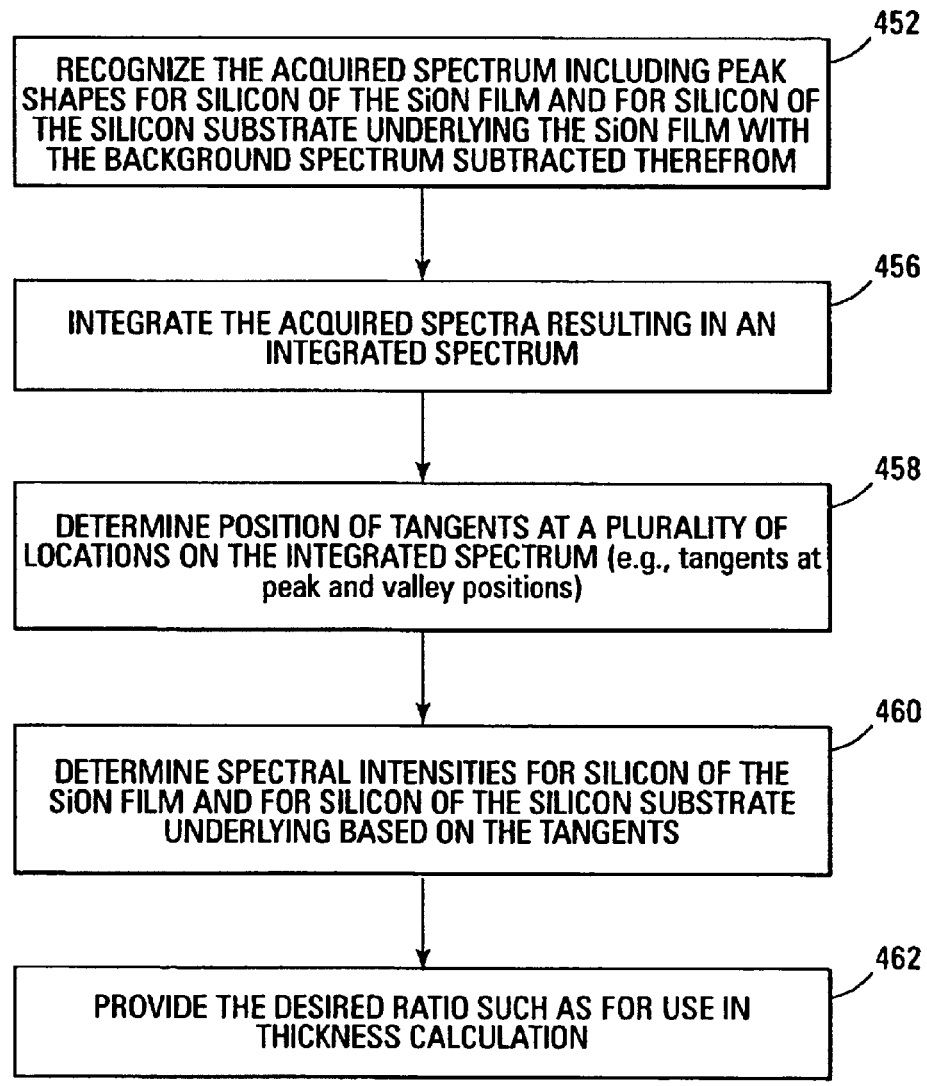
FIG. 12 is one exemplary embodiment of a portion of the method shown generally in FIG. 11.

FIG. 12 shows a flow diagram for one illustrative tangent intersection method 450 used to extract the spectral intensity ratio as described generally with reference to block 406 in FIG. 11. The tangent intersection method 450 provides for recognition of the acquired spectrum 471 including spectral peak shapes 472, 474 representative of the content of silicon in the silicon oxynitride film and the representative of the silicon content of the silicon substrate underlying the silicon oxynitride film, respectively (block 452). The acquired spectrum recognized has already had the spectral background subtracted therefrom.

Figure 13:
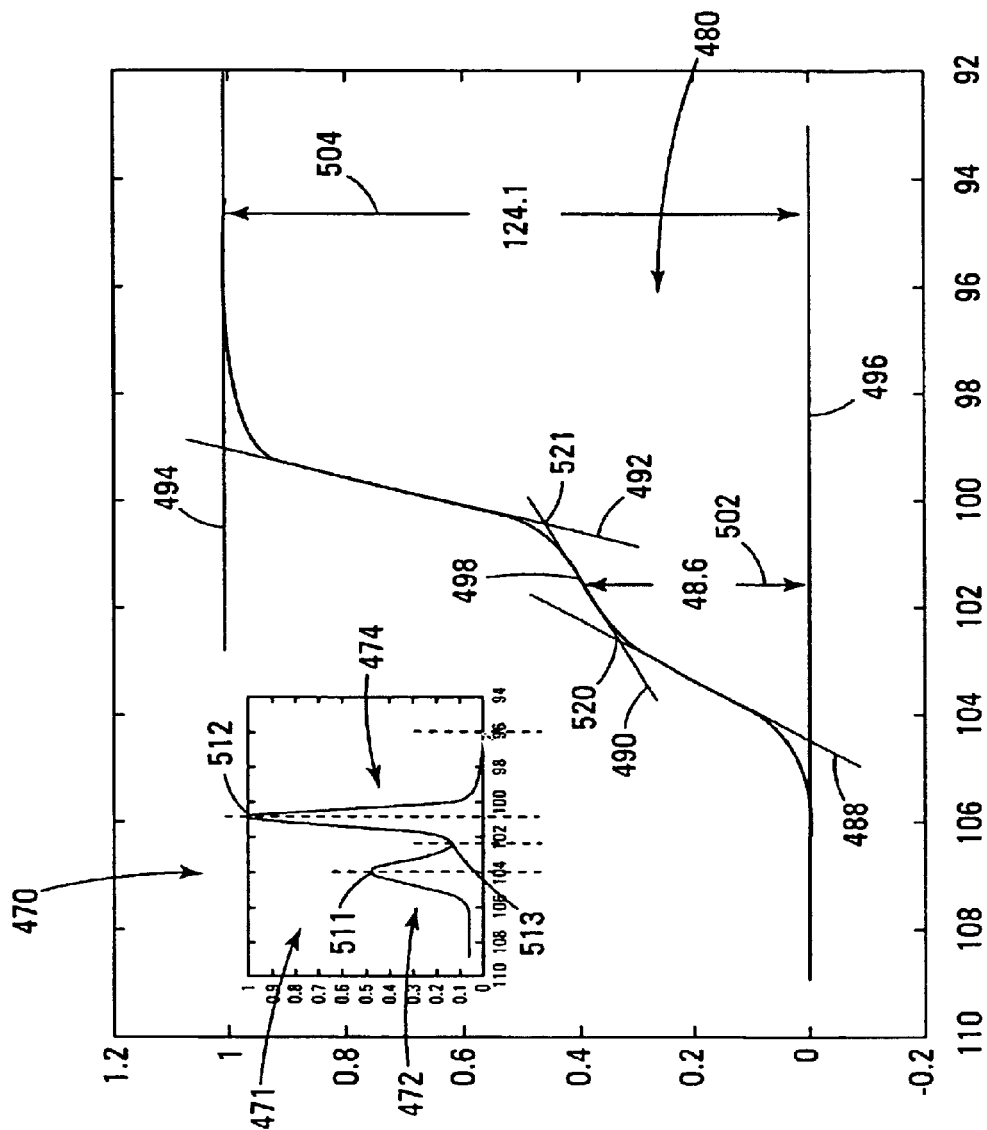
FIG. 13 is a diagram for use in illustrating the methods described in FIGS. 11 and 12.

With the acquired spectrum so recognized (block 452), the spectrum 471 is cumulatively integrated (block 456) resulting in an integrated spectrum 480 as illustrated in FIG. 13. In other words, the Si2p spectrum region is integrated in a cumulative manner. Each point in the integrated spectrum 480 equals the sum of the corresponding point in the acquired spectrum 471 and all points in the acquired spectrum 471 to higher binding energy.

Thereafter, geometric properties of the cumulatively integrated spectrum 480 are used to extract the ratio of spectral intensities. First, positions of multiple tangents are determined for a plurality of locations of the integrated spectrum 480 (block 458). In other words, for example, tangents are provided on the integrated spectrum 480 at multiple positions. A first tangent 488 is provided on the integrated spectrum 480 at the position of the peak 511 of peak shape 472 of the acquired spectrum 471. A second tangent 492 is provided on the integrated spectrum 480 at the position of the peak 512 of the peak shape 474 of the acquired spectrum 471. A third tangent 490 is provided on the integrated spectrum 480 at the position of minimum intensity 513 between the peak 511 and 512 of the acquired spectrum 471. Further, a horizontal line 494 is provided tangent to the maximum of the integral 480 and likewise a horizontal baseline 496 is provided tangent to the integral at its minimum. Preferably, the tangents and slopes thereof may all be determined by the algorithm and require no operator input.

The spectral intensity of peak area 472 and the peak area 474 (and thus the ratio of such spectral intensities) can then be determined based on the tangents (block 460). The spectral intensity of peak area 472 representative of the silicon content in the silicon oxynitride film is determined from the intersections 520, 521 of the tangents 488, 492, and 490 at the peak and valley positions.

A division point 498, which divides the integral into its two components corresponding to the two peak areas 472 and 474, lies between the two intersections 520, 521 and is representative of the integrated spectral intensity of peak area 472. The division point 498 may be the midpoint on the energy axis between the two intersections or some other fraction of the distance between the intersections. In other words, a measured value 502 from baseline "0" to the division point 498 is representative of the spectral intensity of the peak area 472 (e.g., 48.6 as shown in FIG. 13).

The spectral intensity of peak area 474 representative of the silicon content in the silicon substrate upon which the silicon oxynitride film is formed is given by the difference between the total spectral intensity of both the peak areas 472, 474 and the spectral intensity of peak area 472 determined as described above. In other words, the total spectral intensity of both the peak areas 472, 474 is represented by the measured value or height from baseline "0" to the position of horizontal line 494 at the maximum on the integrated spectrum 480 (e.g., 124.1 as shown in FIG. 13). As such, the spectral intensity of peak area 474 representative of the silicon content in the silicon substrate upon which the silicon oxynitride film is formed in the illustrative diagram of FIG. 13 is given by the difference between 124.1 and 48.6. With such spectral intensities known, the desired ratio of spectral intensities, such as for use in the calculation of film thickness, can be provided (block 462).

Further, it may be beneficial to smooth the acquired spectrum 471 before applying the algorithm. Alternatively, the integrated spectrum 480 may be smoothed before applying the algorithm. Smoothing processes are known to those skilled in the art and will not be described in any detail herein.

Further, in the determination of thickness, the constants of the thickness equation (e.g., $\lambda$ and K) may be adjusted to account for the fact that the values for the spectral intensities may not be exactly equivalent to those determined by other methods (e.g., fitting methods).

Figure 4:
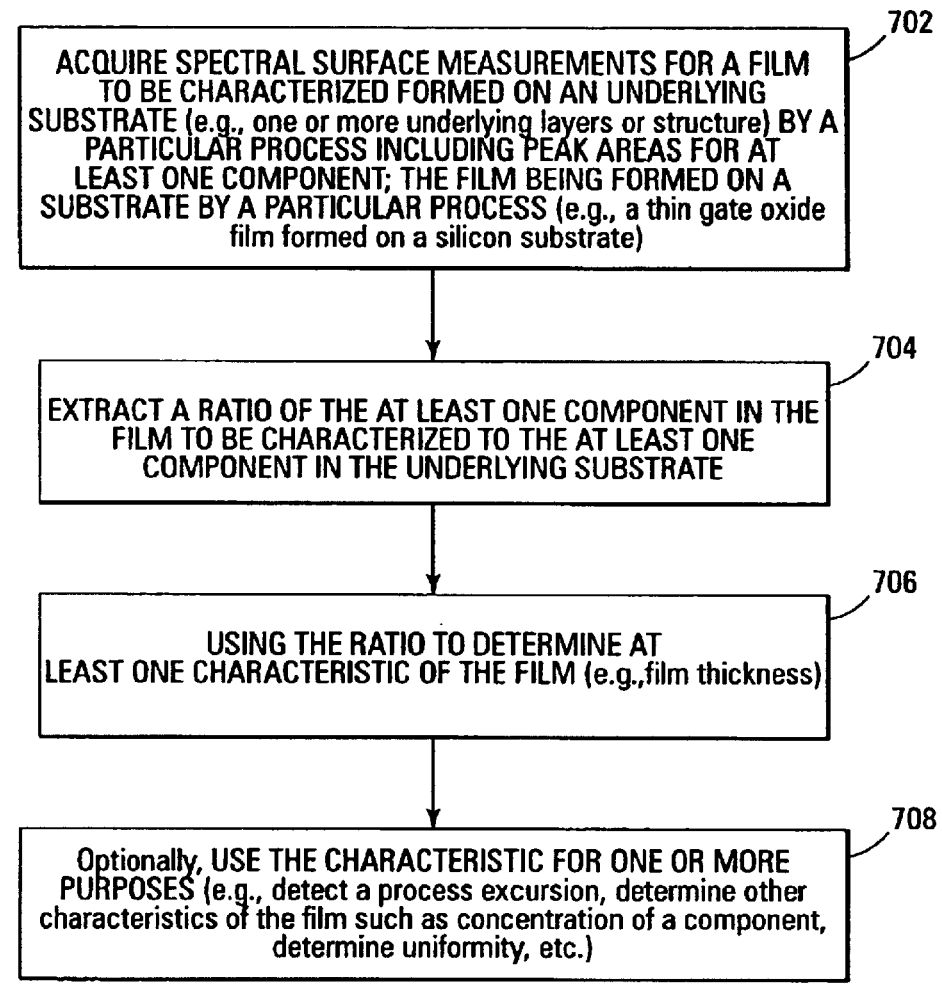
FIG. 4 is an exemplary diagram of one embodiment of a film characterization method that is illustrative of both the methods shown in FIGS. 2 and 3.

It will be recognized that the embodiments of the present invention as described with reference to FIG. 2 (including the exemplary embodiments described with reference to FIGS. 8–10) and FIG. 3 (including the exemplary embodiments described with reference to FIGS. 11–13) are representative of a more general characterization method 700 shown in FIG. 4. As shown in FIG. 4, the method 700 includes acquiring spectral surface measurements to provide an acquired spectrum for a film to be characterized (block 702). The film being characterized is formed on an underlying substrate by a particular process. The acquired spectrum includes at least one or more peak areas for at least one component of interest in the film.

A ratio of the concentration of the at least one component in the film to the concentration of the at least one component in the underlying substrate is extracted using one or more different methods (block 704). For example, the ratio may be extracted using a fitting process and measured basis spectra as described with reference to FIGS. 2 and 8–10. Alternatively, for example, the ratio may be extracted by consideration of a cumulatively integrated acquired spectrum, such as generally described with reference to FIG. 3 and more specifically with reference to FIGS. 11–13.

Thereafter, the ratio may be used to determine at least on characteristic of the film (block 706). For example, thickness may be determined as described herein. Likewise, as described elsewhere herein, the characteristic may optionally be used for one or more other purposes (block 708), such as, for example, detection of a process excursion.

Figure 14:
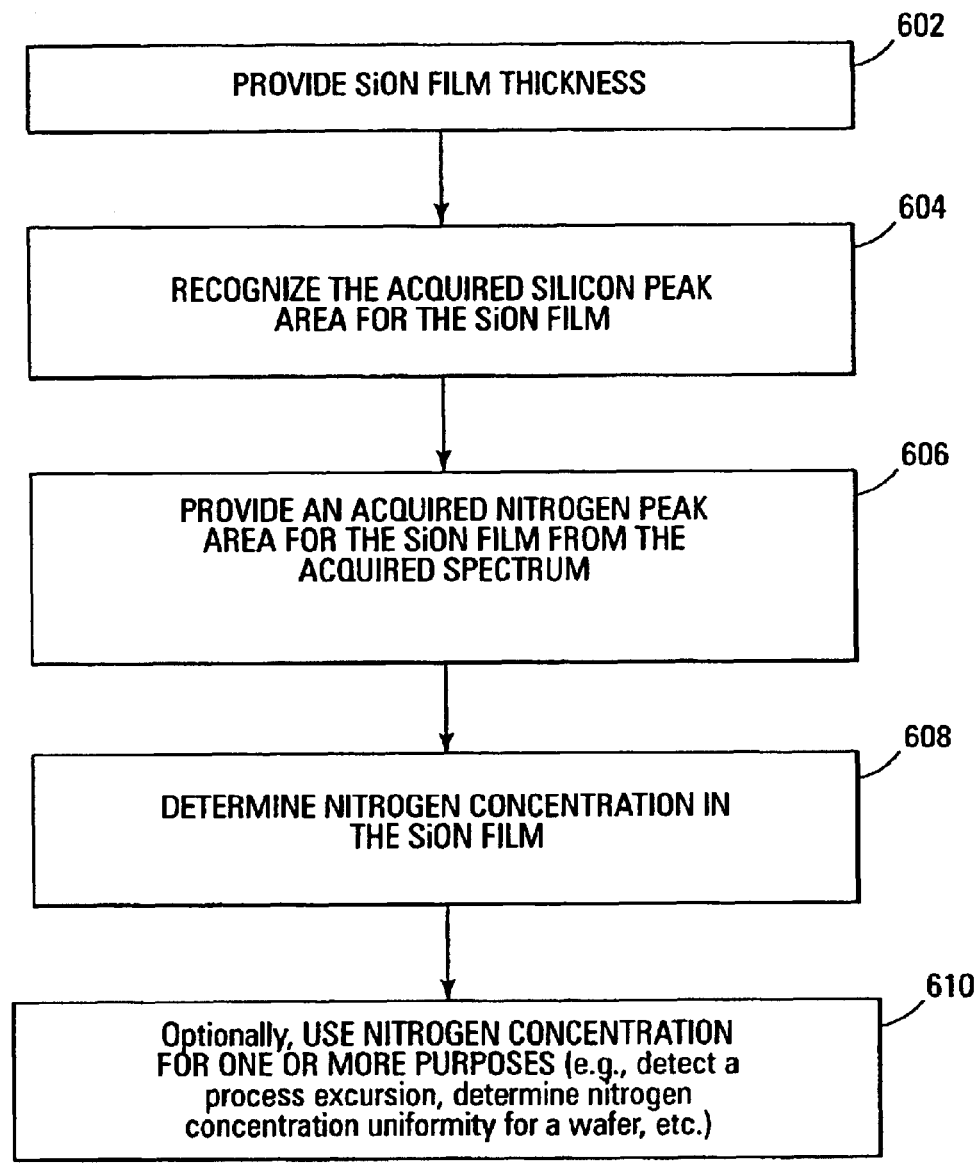
FIG. 14 is an illustrative flow diagram of one embodiment of a concentration determination process using film thickness such as determined as illustratively shown in FIGS. 8A and 11.
Figure 15:
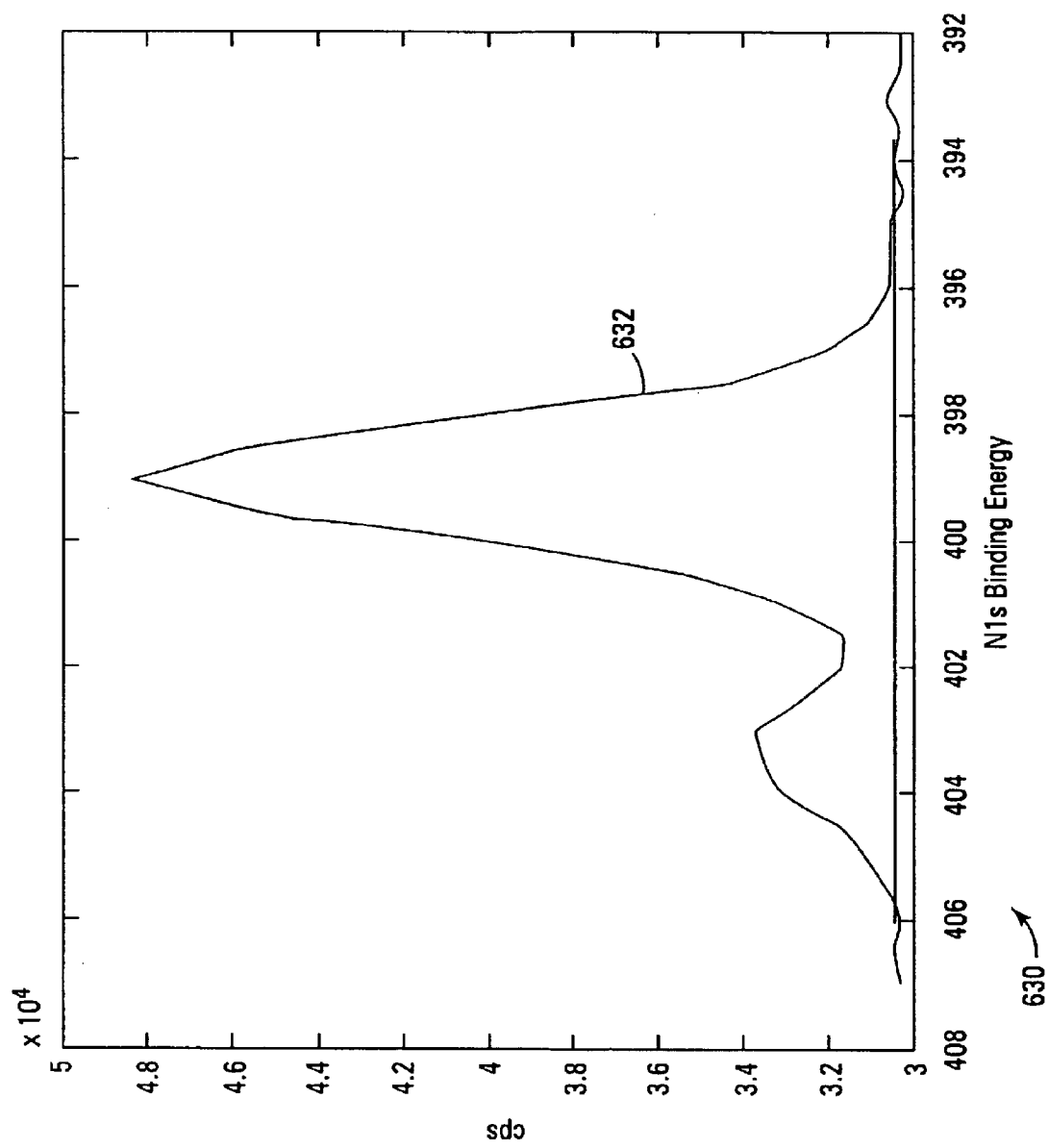
FIG. 15 is an illustrative diagram for use in describing the process shown generally in FIG. 14.

FIG. 14 shows a block diagram of a concentration determination process 600 for determining nitrogen concentration in a silicon oxynitride film to be characterized, using the following equation:

$$\text{Nitrogen Dose} = (\text{Si}^{+4}\text{atoms}/(\text{cm}^2\text{Å}))(\text{N\%}/\text{Si}^{+4}\text{\%})(\text{film thickness Å})$$

The equation above determines N dose using three components: the density of $\text{Si}^{+4}$ atoms in $\text{SiO}_2$, a known physical property; the ratio of the atomic concentration of N and $\text{Si}^{+4}$ detected in the measurement; and the film thickness. As shown in the above nitrogen dose equation, film thickness, such as determined using one or more processes as described herein, plays a role in determining the nitrogen dose.

The process 600 for determining the nitrogen concentration in the silicon oxynitride film includes providing silicon oxynitride film thickness (block 602). As indicated above, this silicon oxynitride film thickness may be provided in a manner as described with reference to FIGS. 8–13 or in any other manner. Further, the process 600 recognizes the acquired silicon peak area for the silicon oxynitride film also as previously described herein (block 604).

Further, an acquired nitrogen peak area for the silicon oxynitride film from the acquired spectra is also provided (block 606). An exemplary acquired nitrogen peak area 632 is shown in the spectra diagram 630 of FIG. 15. As the substrate is a silicon substrate upon which the silicon oxynitride film to be characterized is formed, the nitrogen peak area 632 is representative of the abundance of the nitrogen in the silicon oxynitride film.

With the peak area for nitrogen and peak area for silicon provided, along with a film thickness measurement, the concentration determination process 600 may determine nitrogen concentration at a spot of the silicon oxynitride film (block 608) in accordance with the nitrogen dose equation provided herein.

Optionally, the nitrogen concentration may be used for one or more various purposes (block 610). For example, and as previously mentioned herein, a process excursion may be detected if such nitrogen concentration deviates from a predetermined limit or changes by a predetermined amount. A change in the calculated nitrogen concentration indicates either a true change in nitrogen concentration in the film or a change in the nitrogen concentration versus depth distribution in the film. In other words, the present invention is sensitive to both a change in nitrogen concentration and a change in the nitrogen depth distribution, or both.

Further, the nitrogen concentration determination process may be repeated at various locations of the wafer to provide for the determination of nitrogen concentration uniformity across a wafer. For example, in addition to determining the nitrogen at a spot of the thin silicon oxynitride film, rastering or scanning of the x-ray beam can be used to provide measurements from a relatively larger spot region, e.g., $(1.5 \text{ mm})^2$, while the sample can be moved to provide measurements over a larger area, e.g., a wafer, disc media, etc. As such, nitrogen content can be determined for the larger area across the thin film. With the nitrogen content known, the degree of nitrogen uniformity in the film can be determined, e.g., uniformity of nitrogen distribution across a wafer having the film to be analyzed formed thereon.

As discussed generally herein, with various characteristics of the film being generated non-invasively, one or more processes can be controlled based thereon. For example, as previously described herein, the analysis system can be interfaced to production tools used to fabricate the thin films.

All patents and references disclosed herein are incorporated by reference in their entirety, as if individually incorporated. The preceding specific embodiments are illustrative of the practice of the present invention. It is to be understood, therefore, that other expedients known to those skilled in the art or disclosed herein may be employed without departing from the invention or the scope of the appended claims.

What is claimed is:

1. A method for use in characterizing a film, the method comprising:
    providing at least one measured spectral peak shape representative of a concentration of at least one component of a film, wherein the film is formed on a substrate by a particular process defined by a set of processing conditions, wherein providing the at least one measured spectral peak shape comprises:
        providing a measured spectral peak shape representative of a concentration of the at least one component in the film; and
        providing at least another measured spectral peak shape representative of a concentration of the at least one component in at least a portion of the substrate;
    providing an acquired spectrum for an additional film to be characterized, wherein the acquired spectrum comprises overlapping peak areas representative of a concentration of the at least one component in the additional film and the at least one component in at least a portion of the substrate, wherein the additional film is formed on a substrate by the particular process defined by the set of processing conditions;

comparing the at least one measured spectral peak shape to the acquired spectrum, wherein comparing the at least one measured spectral peak shape to the acquired spectrum comprises fitting the acquired spectrum to the measured spectral peak shape representative of a concentration of the at least one component in the film and the at least another measured spectral peak shape representative of a concentration of the at least one component in at least a portion of the substrate to extract separate acquired spectrum peak areas from the overlapping peak areas; and determining at least a thickness measurement for the film to be characterized based on the comparison.

2. The method of claim 1, wherein the method further comprises calculating at least one spectral background for the acquired spectrum and further wherein comparing the at least one measured spectral peak shape to the acquired spectrum comprises comparing the at least one measured spectral peak shape and the spectral background to the acquired spectrum.

3. The method of claim 2, wherein comparing the at least one measured spectral peak shape and the spectral background to the acquired spectrum comprises fitting the acquired spectrum to the measured spectral peak shape representative of a concentration of the at least one component in the film and the at least another measured spectral peak shape representative of a concentration of the at least one component in at least a portion of the substrate using the spectral background calculated from the acquired spectrum to extract separate acquired spectrum peak areas from the overlapping peak areas, wherein one of the separate acquired spectrum peak areas is representative of a concentration of the at least one component in the additional film and the another separate acquired spectrum peak area is representative of the at least one component in at least a portion of the substrate.

4. The method of claim 1, wherein providing the at least one measured spectral peak shape comprises:

providing a high resolution spectrum for the film;

subtracting a spectral background from the high resolution spectrum;

separating at least one narrow measured spectral peak shape representative of a concentration of at least one component of the film and at least another narrow measured spectral peak shape representative of a concentration of the at least one component in at least a portion of the substrate; and applying a broadening function to the at least one narrow measured spectral peak shape and the at least another narrow measured spectral peak shape to match a resolution of the acquired spectrum.

5. The method of claim 1, wherein the method further comprises determining a concentration of a component of the additional film based at least on the thickness measurement.

6. The method of claim 5, wherein the method further comprises repeating the determination of a concentration of a component of the additional film at a plurality of locations across the additional film for use in determining a degree of uniformity of concentration of the component across the additional film.

7. The method of claim 1, wherein the method further comprises repeating the determination of a thickness measurement at a plurality of locations of the additional film for use in determining a degree of uniformity of thickness across the additional film.

8. The method of claim 1, wherein the method further comprises detecting a process excursion associated with the particular process based on the thickness measurement.

9. The method of claim 1, wherein providing at least one measured spectral peak shape representative of a concentration of at least one component of a film and providing the acquired spectrum for the additional film to be characterized comprises performing one or more surface spectral measurements for the film and the additional film using a particular set of parameters, wherein providing the surface spectral measurements comprises:

irradiating the additional film with x-rays resulting in the escape of photoelectrons;

detecting the escaping photoelectrons; and generating a signal representative of the detected photoelectrons, wherein the surface spectral measurements are based on the generated signal.

10. The method of claim 9, wherein detecting the escaping photoelectrons comprises:

providing an analyzer comprising an input lens receptive of photoelectrons, the input lens having a central axis extending therethrough; and positioning the input lens such that the central axis of the input lens is at an analyzer angle relative to a surface of the additional film, wherein the analyzer angle is in the range of about 45 degrees to about 90 degrees.

11. The method of claim 10, wherein the analyzer angle is in the range of about 60 degrees to about 90 degrees.

12. The method of claim 9, wherein irradiating the additional film with x-rays comprises irradiating the additional film with x-rays from a low energy x-ray source less than 2000 eV.

13. The method of claim 1, wherein each of the film and the additional film comprise a dielectric film.

14. The method of claim 13, wherein each of the film and the additional film comprise a thin film having a thickness of less than about 10 nanometers.

15. The method of claim 14, wherein each of the film and the additional film comprise a thin film having a thickness of less than about 4 nanometers.

16. The method of claim 13, wherein each of the film and the additional film comprise a film comprising silicon, oxygen and nitrogen formed on a substrate comprising silicon, and further wherein the at least one measured spectral peak shape is representative of a concentration of silicon.

17. The method of claim 1, wherein providing the at least one measured spectral peak shape comprises providing a measured spectral peak shape representative of a concentration of silicon in the film and providing at least another measured spectral peak shape representative of a concentration of the silicon in at least a portion of the substrate, wherein the acquired spectrum comprises overlapping peak areas representative of a concentration of silicon in the additional film and in at least a portion of the substrate, and further wherein comparing the at least one measured spectral peak shape to the acquired spectrum comprises fitting the acquired spectrum to the measured spectral peak shape representative of a concentration of silicon in the film and the at least another measured spectral peak shape representative of a concentration of silicon in at least a portion of the substrate using the spectral background calculated from the acquired spectrum to extract separate acquired spectrum peak areas from the overlapping peak areas, wherein one of the separate acquired spectrum peak areas is representative of a concentration of the silicon in the additional film and another separate acquired spectrum peak area is representative of a concentration of silicon in at least a portion of the substrate.

18. The method of claim 17, wherein determining a thickness measurement for the additional film comprises determining a thickness measurement for a film comprising silicon, oxygen and nitrogen based on the comparison.

19. The method of claim 18, wherein the method further comprises determining a concentration of nitrogen in the additional film based at least on the thickness measurement and an additional acquired spectrum representative of nitrogen in the additional film.

20. The method of claim 19, wherein the method further comprises detecting a process excursion associated with the particular process based on the nitrogen concentration.

21. The method of claim 19, wherein the method further comprises determining a degree of uniformity of thickness of the additional film comprising silicon, oxygen and nitrogen across the additional film or a degree of uniformity of the concentration of nitrogen across the additional film.

22. A method for use in characterizing a film, the method comprising:
    providing a measured spectral peak shape representative of a concentration of silicon in a film, wherein the film comprises at least silicon and oxygen formed on a substrate comprising silicon, wherein the film is formed on the substrate by a particular process defined by a set of processing conditions;
    providing at least another measured spectral peak shape representative of a concentration of the silicon in at least a portion of the substrate;
    providing an acquired spectrum for an additional film to be characterized, wherein the additional film comprises at least silicon and oxygen formed on a substrate comprising silicon, wherein the additional film is formed on the substrate by the particular process defined by the set of processing conditions, and further wherein the acquired spectrum comprises overlapping peak areas representative of a concentration of silicon in the additional film and in at least a portion of the substrate;
    fitting the acquired spectrum to the measured spectral peak shape representative of a concentration of silicon in the film and the at least another measured spectral peak shape representative of a concentration of silicon in at least a portion of the substrate using a spectral background calculated from the acquired spectrum to extract separate acquired spectrum peak areas from the overlapping peak areas, wherein one of the separate acquired spectrum peak areas is representative of a concentration of the silicon in the additional film and another separate acquired spectrum peak area is representative of a concentration of silicon in at least a portion of the substrate; and
    determining at least a thickness measurement for the additional film based on the separate acquired spectrum peak areas.

23. The method of claim 22, wherein the method comprises calculating spectral background during each cycle of fitting the acquired spectrum to the measured spectral peak shape and the at least another measured spectral peak shape.

24. The method of claim 22, wherein providing a measured spectral peak shape and providing at least another measured spectral peak shape comprises:
    providing a high resolution spectrum for the film;
    subtracting a spectral background from the high resolution spectrum;
    separating at least one narrow measured spectral peak shape representative of a concentration of silicon in the film and at least another narrow measured spectral peak shape representative of a concentration of the at least one component in at least a portion of the substrate; and
    applying a broadening function to the at least one narrow measured spectral peak shape and the at least another narrow measured spectral peak shape to match a resolution of the acquired spectrum.

25. The method of claim 22, wherein the method further comprises repeating the determination of a thickness measurement at a plurality of locations of the additional film for use in determining a degree of uniformity of thickness across the additional film.

26. The method of claim 22, wherein the film and the additional film comprises at least silicon, oxygen, and nitrogen, and further wherein the method comprises determining a concentration of nitrogen in the additional film based at least on the thickness measurement and an additional acquired spectrum representative of nitrogen in the additional film.

27. The method of claim 26, wherein the method further comprises determining a degree of uniformity of thickness of the additional film across the additional film or a degree of uniformity of the concentration of nitrogen across the additional film.

28. The method of claim 26, wherein the method further comprises detecting a process excursion associated with the particular process based on the nitrogen concentration.

29. The method of claim 22, wherein the method further comprises detecting a process excursion associated with the particular process based on the thickness measurement.

30. The method of claim 22, wherein each of the film and the additional film comprise a thin film having a thickness of less than about 10 nanometers.

31. The method of claim 30, wherein each of the film and the additional film comprise a thin film having a thickness of less than about 4 nanometers.

32. A system for use in characterizing a film, wherein the system comprises:
    an x-ray source operable to irradiate one or more films with x-rays resulting in the escape of photoelectrons;
    an analyzer operable to detect escaping photoelectrons, wherein the analyzer is operable to generate a signal representative of the detected photoelectrons for use in providing an acquired spectrum for one or more films; and
    a computing apparatus operable to:
        recognize at least one measured spectral peak shape representative of a concentration of at least one component of a film, wherein the film is formed on a substrate by a particular process defined by a set of processing conditions, wherein the at least one measured spectral peak shape comprises a measured spectral peak shape representative of a concentration of the at least one component in the film and at least another measured spectral peak shape representative of a concentration of the at least one component in at least a portion of the substrate;
        recognize an acquired spectrum for an additional film to be characterized, wherein the acquired spectrum comprises overlapping peak areas representative of a concentration of the at least one component in the additional film and the at least one component in at least a portion of the substrate, wherein the additional film is formed on a substrate by the particular process defined by the set of processing conditions;

compare the at least one measured spectral peak shape to the acquired spectrum by fitting the acquired spectrum to the measured spectral peak shape representative of a concentration of the at least one component in the film and the at least another measured spectral peak shape representative of a concentration of the at least one component in at least a portion of the substrate to extract separate acquired spectrum peak areas from the overlapping peak areas; and determine at least a thickness measurement based on the comparison.

33. The system of claim 32, wherein the computing apparatus is further operable to calculate at least one spectral background for the acquired spectrum and further wherein the computing apparatus is operable to compare the at least one measured spectral peak shape and the spectral background to the acquired spectrum.

34. The system of claim 33, wherein the computing apparatus is operable to compare the at least one measured spectral peak shape to the acquired spectrum by fitting the acquired spectrum to the measured spectral peak shape representative of a concentration of the at least one component in the film and the at least another measured spectral peak shape representative of a concentration of the at least one component in at least a portion of the substrate using the spectral background calculated from the acquired spectrum to extract separate acquired spectrum peak areas from the overlapping peak areas, wherein one of the separate acquired spectrum peak areas is representative of a concentration of the at least one component in the additional film and the another separate acquired spectrum peak area is representative of the at least one component in at least a portion of the substrate.

35. The system of claim 32, wherein the computing apparatus is further operable to provide the measured spectral peak shape representative of a concentration of the at least one component in the film and the at least another measured spectral peak shape representative of a concentration of the at least one component in at least a portion of the substrate by:

recognizing a high resolution spectrum for a film formed on a substrate by the particular process defined by the set of processing conditions;

subtracting a spectral background from the high resolution spectrum;

separating at least one narrow measured spectral peak shape representative of a concentration of at least one component of a film and at least another narrow measured spectral peak shape representative of a concentration of the at least one component in at least a portion of the substrate; and applying a broadening function to the at least one narrow measured spectral peak shape and the at least another narrow measured spectral peak shape to match a resolution of the acquired spectrum.

36. The system of claim 32, wherein the computing apparatus is further operable to determine a concentration of a component of the additional film based at least on the thickness measurement.

37. The system of claim 32, wherein the computing apparatus is further operable to detect a process excursion associated with the particular process based on at least the thickness measurement.

38. The system of claim 32, wherein the analyzer comprises an input lens receptive of photoelectrons, the input lens having a central axis extending therethrough, wherein the input lens is positioned such that the central axis of the input lens is at an analyzer angle relative to a surface of the one or more films, wherein the analyzer angle is in the range of about 45 degrees to about 90 degrees.

39. The system of claim 38, wherein the analyzer angle is in the range of about 60 degrees to about 90 degrees.

40. The system of claim 32, wherein the x-ray source is a low energy x-ray source less than 2000 eV.

41. The system of claim 32, wherein the additional film comprises at least silicon and oxygen formed on a substrate comprising silicon, wherein the acquired spectrum comprises overlapping peak areas representative of a concentration of silicon in the additional film and in at least a portion of the substrate, and further wherein the computing apparatus is operable to:

recognize a measured spectral peak shape representative of a concentration of silicon in a film, wherein the film comprises at least silicon and oxygen formed on a substrate comprising silicon;

recognize at least another measured spectral peak shape representative of a concentration of silicon in at least a portion of the substrate; and calculate at least one spectral background for the acquired spectrum.

42. The system of claim 41, wherein the computing apparatus is further operable to compare the at least one measured spectral peak shape to the acquired spectrum by fitting the acquired spectrum to the measured spectral peak shape representative of a concentration of silicon in the film and the at least another measured spectral peak shape representative of a concentration of silicon in at least a portion of the substrate using the spectral background calculated from the acquired spectrum to extract separate acquired spectrum peak areas from the overlapping peak areas, wherein one of the separate acquired spectrum peak areas is representative of a concentration of silicon in the additional film and the another separate acquired spectrum peak area is representative of silicon in at least a portion of the substrate.

43. The system of claim 32, wherein the computing apparatus is further operable to recognize the determination of a thickness measurement at a plurality of locations of the additional film for use in determining a degree of uniformity of thickness across the additional film.

44. The system of claim 32, wherein the film and the additional film comprise at least silicon, oxygen, and nitrogen, and further wherein the computing apparatus is further operable to determine a concentration of nitrogen in the additional film based at least on the thickness measurement and an additional acquired spectrum representative of nitrogen in the additional film.

45. The system of claim 44, wherein the computing apparatus is further operable to recognize the determination of a concentration of nitrogen in the additional film at a plurality of locations across the additional film for use in determining a degree of uniformity of concentration of the component across the additional film.

46. The system of claim 44, wherein the computing apparatus is further operable to detect a process excursion associated with the particular process based on the nitrogen concentration.

47. A program storage media, readable by a media read apparatus under control of a computer, tangibly embodying a program executable to perform a process for characterization of thin films, wherein the program is operable to:

recognize at least one measured spectral peak shape representative of a concentration of at least one component of a film, wherein the film is formed on a substrate by a particular process defined by a set of processing conditions, and wherein the at least one measured spectral peak shape comprises a measured spectral peak shape representative of a concentration of the at least one component in the film and at least another measured spectral peak shape representative of a concentration of the at least one component in at least a portion of the substrate;

recognize an acquired spectrum for an additional film to be characterized, wherein the acquired spectrum comprises overlapping peak areas representative of a concentration of the at least one component in the additional film and the at least one component in at least a portion of the substrate, and further wherein the additional film is formed on a substrate by the particular process defined by the set of processing conditions;

compare the at least one measured spectral peak shape to the acquired spectrum by fitting the acquired spectrum to the measured spectral peak shape representative of a concentration of the at least one component in the film and the at least another measured spectral peak shape representative of a concentration of the at least one component in at least a portion of the substrate to extract separate acquired spectrum peak areas from the overlapping peak areas; and determine at least one thickness measurement for the additional film based on the comparison.

48. The program storage media of claim 47, wherein the program is further operable to calculate at least one spectral background for the acquired spectrum and further wherein the computing apparatus is operable to compare the at least one measured spectral peak shape and the spectral background to the acquired spectrum.

49. The program storage media of claim 48, wherein the program is operable to compare the at least one measured spectral peak shape to the acquired spectrum by fitting the acquired spectrum to the measured spectral peak shape representative of a concentration of the at least one component in the film and the at least another measured spectral peak shape representative of a concentration of the at least one component in at least a portion of the substrate using the spectral background calculated from the acquired spectrum to extract separate acquired spectrum peak areas from the overlapping peak areas, wherein one of the separate acquired spectrum peak areas is representative of a concentration of the at least one component in the additional film and the another separate acquired spectrum peak area is representative of the at least one component in at least a portion of the substrate.

50. The program storage media of claim 47, wherein the program is further operable to provide the measured spectral peak shape representative of a concentration of the at least one component in the film and the at least another measured spectral peak shape representative of a concentration of the at least one component in at least a portion of the substrate by:

recognizing a high resolution spectrum for the film;

subtracting a spectral background from the high resolution spectrum;

separating at least one narrow measured spectral peak shape representative of a concentration of at least one component of the film and at least another narrow measured spectral peak shape representative of a concentration of the at least one component in at least a portion of the substrate; and applying a broadening function to the at least one narrow measured spectral peak shape and the at least another narrow measured spectral peak shape to match a resolution of the acquired spectrum.

51. The program storage media of claim 47, wherein the program is further operable to determine a concentration of a component of the additional film based at least on the thickness measurement.

52. The program storage media of claim 51, wherein the program is further operable to recognize the determination of a concentration of a component of the additional film at a plurality of locations across the additional film for use in determining a degree of uniformity of concentration of the component across the additional film.

53. The program storage media of claim 47, wherein the program is further operable to recognize the determination of a thickness measurement at a plurality of locations of the additional film for use in determining a degree of uniformity of thickness across the additional film.

54. The program storage media of claim 47, wherein the program is further operable to detect a process excursion associated with the particular process based on the at least one thickness measurement.

55. The program storage media of claim 47, wherein the at least one measured spectral peak shape is representative of a concentration of silicon in the film.

* * * * *